(12) United States Patent
Gray et al.

(10) Patent No.: US 12,011,364 B2
(45) Date of Patent: Jun. 18, 2024

(54) EXPANDABLE FOOTPRINT IMPLANT

(71) Applicant: GLOBUS MEDICAL, INC., Audubon, PA (US)

(72) Inventors: Jason Gray, East Greenville, PA (US); John LaColla, West Chester, PA (US); George Howard, Green Lane, PA (US)

(73) Assignee: Globus Medical, Inc, Audubon, PA (US)

( * ) Notice: Subject to any disclaimer, the term of this patent is extended or adjusted under 35 U.S.C. 154(b) by 0 days.

(21) Appl. No.: 17/841,118

(22) Filed: Jun. 15, 2022

(65) Prior Publication Data

US 2023/0404770 A1    Dec. 21, 2023

(51) Int. Cl.
*A61F 2/44* (2006.01)
*A61F 2/46* (2006.01)
*A61F 2/30* (2006.01)

(52) U.S. Cl.
CPC .......... *A61F 2/4455* (2013.01); *A61F 2/4611* (2013.01); *A61F 2002/30476* (2013.01); *A61F 2002/30556* (2013.01); *A61F 2002/30579* (2013.01)

(58) Field of Classification Search
CPC ...... A61F 2/4455; A61F 2/446; A61F 2/4465; A61F 2/447; A61F 2002/30556; A61F 2002/30266; A61F 2002/30555; A61F 2002/30545
See application file for complete search history.

(56) References Cited

U.S. PATENT DOCUMENTS

| | | |
|---|---|---|
| 4,349,921 A | 9/1982 | Kuntz |
| 4,599,086 A | 7/1986 | Doty |
| 4,863,476 A | 9/1989 | Shepperd |
| 4,863,477 A | 9/1989 | Monson |
| 5,123,926 A | 6/1992 | Pisharodi |
| 5,290,312 A | 3/1994 | Kojimoto et al. |
| 5,306,310 A | 4/1994 | Siebels |
| 5,375,823 A | 12/1994 | Navas |
| 5,390,683 A | 2/1995 | Pisharodi |
| 5,522,899 A | 6/1996 | Michelson |
| 5,534,030 A | 7/1996 | Navarro et al. |
| 5,554,191 A | 9/1996 | Lahille et al. |
| 5,571,192 A | 11/1996 | Schonhoffer |
| 5,645,596 A | 7/1997 | Kim |
| 5,653,763 A | 8/1997 | Errico et al. |

(Continued)

FOREIGN PATENT DOCUMENTS

| | | |
|---|---|---|
| CA | 2088066 A1 | 1/1992 |
| DE | 4012622 C1 | 7/1991 |

(Continued)

*Primary Examiner* — Jan Christopher L Merene

(57) ABSTRACT

Expandable fusion implants capable of being installed inside an intervertebral disc space to maintain disc spacing and restore spinal stability, thereby facilitating an intervertebral fusion. The expandable intervertebral implant may be configured to transition from a collapsed configuration having a first width and a first height to an expanded configuration having a second width and a second height. The implant may include front and rear plates each having horizontal ramps configured to interface with corresponding horizontal ramps on actuators and front ramps of left and/or right side portion assemblies.

14 Claims, 16 Drawing Sheets

(56) References Cited

U.S. PATENT DOCUMENTS

| | | |
|---|---|---|
| 5,665,122 A | 9/1997 | Kambin |
| 5,676,701 A | 10/1997 | Yuan et al. |
| 6,039,761 A | 3/2000 | Li et al. |
| 6,045,579 A | 4/2000 | Hochschuler et al. |
| 6,080,193 A | 6/2000 | Hochschuler et al. |
| 6,099,531 A | 8/2000 | Bonutti |
| 6,126,689 A | 10/2000 | Brett |
| 6,176,882 B1 | 1/2001 | Biedermann et al. |
| 6,258,125 B1 | 7/2001 | Paul et al. |
| 6,558,423 B1 | 5/2003 | Michelson |
| 6,562,074 B2 | 5/2003 | Gerbec et al. |
| 6,576,016 B1 | 6/2003 | Hochschuler et al. |
| 6,554,863 B2 | 8/2003 | Paul et al. |
| 6,641,614 B1 | 11/2003 | Wagner et al. |
| 6,648,917 B2 | 11/2003 | Gerbec et al. |
| 6,666,891 B2 | 12/2003 | Boehm, Jr. et al. |
| 6,692,495 B1 | 2/2004 | Zacouto |
| 6,706,070 B1 | 3/2004 | Wagner et al. |
| 6,752,832 B2 | 6/2004 | Ulrich |
| 6,814,756 B1 | 11/2004 | Michelson |
| 6,830,589 B2 | 12/2004 | Erickson |
| 6,849,093 B2 | 2/2005 | Michelson |
| 6,852,129 B2 | 2/2005 | Gerbec et al. |
| 6,863,673 B2 | 3/2005 | Gerbec et al. |
| 6,881,228 B2 | 4/2005 | Zdeblick et al. |
| 7,018,415 B1 | 3/2006 | McKay |
| 7,070,598 B2 | 7/2006 | Lim et al. |
| 7,204,853 B2 | 4/2007 | Gordon |
| 7,217,291 B2 | 5/2007 | Zucherman et al. |
| 7,282,063 B2 | 10/2007 | Cohen et al. |
| 7,316,714 B2 | 1/2008 | Gordon |
| 7,473,276 B2 | 1/2009 | Aebi et al. |
| 7,547,325 B2 | 6/2009 | Biedermann et al. |
| 7,621,953 B2 | 11/2009 | Braddock, Jr. et al. |
| 7,641,693 B2 | 1/2010 | Gutlin et al. |
| 7,682,396 B2 | 3/2010 | Beaurain et al. |
| 7,749,270 B2 | 7/2010 | Peterman |
| 7,753,958 B2 | 7/2010 | Gordon |
| 7,771,473 B2 | 8/2010 | Thramann |
| 7,780,732 B2 | 8/2010 | Abernathie |
| 7,799,081 B2 | 9/2010 | Mckinley |
| 7,815,683 B2 | 10/2010 | Melkent et al. |
| 7,837,734 B2 | 11/2010 | Zucherman et al. |
| 7,875,078 B2 | 1/2011 | Wysocki et al. |
| 7,901,409 B2 | 3/2011 | Canaveral et al. |
| 7,909,869 B2 | 3/2011 | Gordon |
| 7,951,199 B2 | 5/2011 | Miller |
| 7,985,256 B2 | 7/2011 | Grotz et al. |
| 8,062,375 B2 | 11/2011 | Glerum |
| 8,070,813 B2 | 12/2011 | Grotz et al. |
| 8,123,810 B2 | 2/2012 | Gordon |
| 8,137,405 B2 | 3/2012 | Kostuik et al. |
| 8,192,495 B2 | 6/2012 | Simpson et al. |
| 8,303,663 B2 | 11/2012 | Jimenez et al. |
| 8,377,140 B2 | 2/2013 | DeFalco et al. |
| 8,394,129 B2 | 3/2013 | Lopez et al. |
| 8,394,143 B2 | 3/2013 | Grotz et al. |
| 8,435,296 B2 | 5/2013 | Kadaba et al. |
| 8,454,695 B2 | 6/2013 | Grotz et al. |
| 8,647,386 B2 | 2/2014 | Gordon |
| 8,696,751 B2 | 4/2014 | Ashley et al. |
| 8,771,360 B2 | 7/2014 | Jimenez et al. |
| 8,894,710 B2 | 11/2014 | Simpson et al. |
| 8,932,355 B2 | 1/2015 | Grotz et al. |
| 8,940,049 B1 | 1/2015 | JImenez et al. |
| 8,956,413 B2 | 2/2015 | Ashley et al. |
| 8,992,620 B2 | 3/2015 | Ashley et al. |
| 9,028,550 B2 | 5/2015 | Shulock et al. |
| 9,358,125 B2 | 6/2016 | JImenez et al. |
| 9,532,883 B2 | 1/2017 | McLuen et al. |
| 9,622,878 B2 | 4/2017 | Grotz |
| 10,507,116 B2 * | 12/2019 | Shoshtaev ............ A61F 2/4611 |
| 2002/0045945 A1 | 4/2002 | Liu |
| 2002/0068976 A1 | 6/2002 | Jackson |
| 2002/0068977 A1 | 6/2002 | Jackson |
| 2003/0176926 A1 | 9/2003 | Boehm et al. |
| 2004/0030387 A1 | 2/2004 | Landry et al. |
| 2004/0049271 A1 | 3/2004 | Biedermann |
| 2004/0054412 A1 | 3/2004 | Gerbec et al. |
| 2004/0087947 A1 | 5/2004 | Lim et al. |
| 2004/0153065 A1 | 8/2004 | Lim |
| 2005/0021041 A1 | 1/2005 | Michelson |
| 2005/0021145 A1 | 1/2005 | de Villiers et al. |
| 2005/0033432 A1 | 2/2005 | Gordon |
| 2005/0080422 A1 | 4/2005 | Otte et al. |
| 2005/0113916 A1 | 5/2005 | Branch |
| 2005/0149188 A1 | 7/2005 | Cook |
| 2005/0171541 A1 | 8/2005 | Boehm |
| 2005/0251258 A1 | 11/2005 | Jackson |
| 2005/0273171 A1 | 12/2005 | Gordon |
| 2005/0273174 A1 | 12/2005 | Gordon |
| 2005/0278026 A1 | 12/2005 | Gordon |
| 2005/0283244 A1 | 12/2005 | Gordon |
| 2005/0283245 A1 | 12/2005 | Gordon |
| 2006/0004453 A1 | 1/2006 | Bartish, Jr. et al. |
| 2006/0015184 A1 | 1/2006 | Winterbottom et al. |
| 2006/0058878 A1 | 3/2006 | Michelson |
| 2006/0084986 A1 | 4/2006 | Grinberg et al. |
| 2006/0122701 A1 | 6/2006 | Kister |
| 2006/0129244 A1 | 6/2006 | Ensign |
| 2006/0142859 A1 | 6/2006 | Mcluen |
| 2006/0149385 A1 | 7/2006 | Mckay |
| 2006/0195192 A1 | 8/2006 | Gordon et al. |
| 2006/0229729 A1 | 10/2006 | Gordon |
| 2006/0241770 A1 | 10/2006 | Rhoda et al. |
| 2006/0253201 A1 | 11/2006 | Mcluen |
| 2007/0043442 A1 | 2/2007 | Abernathie |
| 2007/0050030 A1 | 3/2007 | Kim |
| 2007/0050032 A1 | 3/2007 | Gittings et al. |
| 2007/0055377 A1 | 3/2007 | Hanson et al. |
| 2007/0191951 A1 | 8/2007 | Branch |
| 2007/0255415 A1 | 11/2007 | Edie et al. |
| 2007/0270963 A1 | 11/2007 | Melkent et al. |
| 2007/0270968 A1 | 11/2007 | Baynham |
| 2008/0021559 A1 | 1/2008 | Thramann |
| 2008/0065222 A1 | 3/2008 | Hamada |
| 2008/0114467 A1 | 5/2008 | Capote et al. |
| 2008/0140207 A1 | 6/2008 | Olmos et al. |
| 2008/0147194 A1 | 6/2008 | Grotz et al. |
| 2008/0161933 A1 | 7/2008 | Grotz et al. |
| 2008/0167657 A1 | 7/2008 | Greenhalgh |
| 2008/0183204 A1 | 7/2008 | Greenhalgh et al. |
| 2008/0221694 A1 | 9/2008 | Warnick et al. |
| 2008/0275455 A1 | 11/2008 | Berry et al. |
| 2008/0281346 A1 | 11/2008 | Greenhalgh et al. |
| 2008/0288073 A1 | 11/2008 | Renganath et al. |
| 2008/0300598 A1 | 12/2008 | Barreiro et al. |
| 2008/0306488 A1 | 12/2008 | Altarac et al. |
| 2008/0319487 A1 | 12/2008 | Fielding et al. |
| 2008/0319549 A1 | 12/2008 | Greenhalgh et al. |
| 2009/0024217 A1 | 1/2009 | Levy et al. |
| 2009/0062833 A1 | 3/2009 | Song |
| 2009/0076616 A1 | 3/2009 | Duggal et al. |
| 2009/0125062 A1 | 5/2009 | Amin |
| 2009/0149956 A1 | 6/2009 | Greenhalgh et al. |
| 2009/0149959 A1 | 6/2009 | Conner et al. |
| 2009/0204218 A1 | 8/2009 | Richelsoph |
| 2009/0222100 A1 | 9/2009 | Cipoletti et al. |
| 2009/0240334 A1 | 9/2009 | Richelsoph |
| 2009/0270989 A1 | 10/2009 | Conner et al. |
| 2009/0281628 A1 | 11/2009 | Oglaza et al. |
| 2009/0292361 A1 | 11/2009 | Lopez |
| 2009/0299478 A1 | 12/2009 | Carls et al. |
| 2009/0312763 A1 | 12/2009 | McCormack |
| 2010/0049324 A1 | 2/2010 | Valdevit |
| 2010/0070041 A1 | 3/2010 | Peterman |
| 2010/0082109 A1 | 4/2010 | Greenhalgh et al. |
| 2010/0145455 A1 | 6/2010 | Simpson et al. |
| 2010/0179657 A1 | 7/2010 | Greenhalgh et al. |
| 2010/0211176 A1 | 8/2010 | Greenhalgh |
| 2010/0222816 A1 | 9/2010 | Gabelberger et al. |
| 2010/0286783 A1 | 11/2010 | Lechmann et al. |
| 2011/0035011 A1 | 2/2011 | Cain |
| 2011/0093074 A1 | 4/2011 | Glerum et al. |

(56) References Cited

U.S. PATENT DOCUMENTS

| | | |
|---|---|---|
| 2011/0160861 A1 | 6/2011 | Jimenez et al. |
| 2011/0172774 A1 | 7/2011 | Varela |
| 2011/0276142 A1 | 11/2011 | Niemiec et al. |
| 2011/0301713 A1 | 12/2011 | Theofilos |
| 2011/0319997 A1 | 12/2011 | Glerum et al. |
| 2012/0035729 A1 | 2/2012 | Glerum et al. |
| 2012/0059470 A1 | 3/2012 | Weiman |
| 2012/0059472 A1 | 3/2012 | Weiman |
| 2012/0109308 A1 | 5/2012 | Lechmann et al. |
| 2012/0130496 A1 | 5/2012 | Duffield et al. |
| 2012/0165945 A1 | 6/2012 | Hansell et al. |
| 2012/0185049 A1 | 7/2012 | Varela |
| 2012/0209386 A1 | 8/2012 | Triplett et al. |
| 2012/0215313 A1 | 8/2012 | Saidha et al. |
| 2012/0226357 A1 | 9/2012 | Varela |
| 2012/0265309 A1 | 10/2012 | Glerum et al. |
| 2012/0277861 A1 | 11/2012 | Steele et al. |
| 2012/0277870 A1 | 11/2012 | Wolters et al. |
| 2012/0323329 A1 | 12/2012 | Jimenez et al. |
| 2012/0330426 A1 | 12/2012 | McLaughlin et al. |
| 2013/0023993 A1 | 1/2013 | Weiman |
| 2013/0023994 A1 | 1/2013 | Glerum |
| 2013/0158663 A1 | 6/2013 | Miller et al. |
| 2013/0158669 A1 | 6/2013 | Sungarian et al. |
| 2013/0197647 A1 | 8/2013 | Wolters et al. |
| 2013/0211526 A1 | 8/2013 | Alheidt et al. |
| 2013/0274883 A1 | 10/2013 | McLuen et al. |
| 2014/0039622 A1* | 2/2014 | Glerum ............... A61F 2/447 623/17.15 |
| 2014/0067071 A1 | 3/2014 | Weiman et al. |
| 2014/0088714 A1 | 3/2014 | Miller et al. |
| 2014/0163683 A1 | 6/2014 | Seifert et al. |
| 2015/0066145 A1 | 3/2015 | Rogers et al. |
| 2015/0088258 A1 | 3/2015 | Jimenez et al. |
| 2015/0134064 A1 | 5/2015 | Grotz et al. |
| 2015/0216676 A1 | 8/2015 | Shulock et al. |
| 2015/0289988 A1 | 10/2015 | Ashley et al. |
| 2015/0374508 A1 | 12/2015 | Sandul |
| 2016/0166396 A1 | 6/2016 | McClintock |
| 2016/0324654 A1 | 11/2016 | Loebl et al. |
| 2017/0000622 A1* | 1/2017 | Thommen ............... A61F 2/447 |
| 2017/0100258 A1 | 4/2017 | Jimenez et al. |
| 2017/0119543 A1 | 5/2017 | Dietzel et al. |
| 2018/0193164 A1* | 7/2018 | Shoshtaev ............. A61F 2/4425 |
| 2019/0269521 A1* | 9/2019 | Shoshtaev ............. A61F 2/4455 |
| 2020/0163775 A1* | 5/2020 | Kim ........................ A61F 2/447 |
| 2021/0137695 A1* | 5/2021 | Huang ................... A61F 2/4455 |
| 2022/0395381 A1* | 12/2022 | Valkoun ................ A61F 2/4455 |

FOREIGN PATENT DOCUMENTS

| | | |
|---|---|---|
| DE | 4327054 C1 | 4/1995 |
| EP | 0576379 B1 | 6/1993 |
| EP | 0610837 B1 | 7/1994 |
| EP | 3111896 A1 | 1/2017 |
| FR | 2794968 A1 | 12/2000 |
| JP | 2000-513263 A | 10/2000 |
| KR | 200290058 Y1 | 9/2002 |
| SU | 1424826 A1 | 9/1988 |
| WO | 9201428 A1 | 2/1992 |
| WO | 9525485 A1 | 9/1995 |
| WO | 1999042062 A1 | 8/1999 |
| WO | 1999066867 A1 | 12/1999 |
| WO | 2002045625 A1 | 6/2002 |
| WO | 2004019829 A1 | 3/2004 |
| WO | 2004069033 A2 | 8/2004 |
| WO | 2006045094 A2 | 4/2006 |
| WO | 2006047587 A2 | 5/2006 |
| WO | 2006113080 A2 | 10/2006 |
| WO | 2008044057 A1 | 4/2008 |
| WO | 2008134515 A1 | 11/2008 |
| WO | 2009114381 A1 | 9/2009 |
| WO | 2010103344 A1 | 9/2010 |
| WO | 2012031267 A1 | 3/2012 |
| WO | 2015009793 A1 | 1/2015 |

* cited by examiner

EXPANDABLE FOOTPRINT IMPLANT

FIELD OF THE INVENTION

The present disclosure generally relates to devices and methods for promoting an intervertebral fusion, and more particularly relates to expandable fusion devices capable of being inserted between adjacent vertebrae to facilitate the fusion process.

BACKGROUND OF THE INVENTION

A common procedure for handling pain associated with intervertebral discs that have become degenerated due to various factors, such as trauma or aging, is the use of intervertebral fusion devices for fusing one or more adjacent vertebral bodies. Generally, to fuse the adjacent vertebral bodies, the intervertebral disc is first partially or fully removed. An intervertebral fusion device is then inserted between neighboring vertebrae to maintain normal disc spacing and restore spinal stability, thereby facilitating an intervertebral fusion.

There are a number of fusion devices and methodologies for accomplishing the intervertebral fusion. These include screw and rod arrangements, solid bone implants, and fusion devices which include a cage or other implant mechanism, which may be packed with bone and/or bone growth inducing substances, for example. These devices are implanted between adjacent vertebral bodies in order to fuse the vertebral bodies together, alleviating the associated pain.

However, there are drawbacks associated with the known conventional fusion devices and methodologies. For example, present methods for installing a conventional fusion device often require that the adjacent vertebral bodies be distracted to restore a diseased disc space to its normal or healthy height prior to implantation of the fusion device. In order to maintain this height once the fusion device is inserted, the fusion device is usually dimensioned larger in height than the initial distraction height. This difference in height can make it difficult for a surgeon to install the fusion device in the distracted intervertebral space.

As such, there exists a need for fusion devices capable of being installed inside an intervertebral disc space at a minimum to no distraction height and for a fusion device that can maintain a normal distance between adjacent vertebral bodies when implanted. In addition, it is desired to address issues with subsidence and sagittal balance as well.

SUMMARY OF THE INVENTION

To meet this and other needs, devices, systems, and methods for performing intervertebral fusion are provided. In particular, expandable intervertebral implants, for example, for posterior spinal surgery may be used to treat a variety of patient indications. The expandable implants are configured to increase the overall footprint size after being inserted into the disc space while also adjusting the lordosis and overall height. The in-situ expandable footprint or surface area is configured to address the subsidence issue and in-situ adjustable lordosis is configured to address the sagittal balance issue.

According to one embodiment, an expandable intervertebral implant includes front and rear plates each having horizontal ramps, a central drive screw for moving the front plate relative to the rear plate, and left and right side portion assemblies. The left and right side portion assemblies each include upper and lower endplates having vertical ramps, an actuator having horizontal ramps slidably engaged with the horizontal ramps of the rear plate and vertical ramps slidably engaged with the vertical ramps of the upper and lower endplates, and a front ramp having horizontal ramps slidably engaged with the horizontal ramps of the front plate and vertical ramps slidably engaged with the vertical ramps of the upper and lower endplates. By rotating the drive screw, the implant expands in width and then in height.

The expandable implant may include one or more of the following attributes. The rear plate may include a pair of female horizontal ramps defined into top and bottom surfaces of the rear plate, and the actuator may include a pair of horizontal male ramps configured to interface with the female horizontal ramps of the rear plate. The horizontal ramps of the rear plate may be slanted such that one end of each ramp starts at a side of the rear plate and extends toward a center of the rear plate with the horizontal ramps leading toward one another. One of the female horizontal ramps may have a depth greater than the other female horizontal ramp. The front plate may include a pair of female horizontal ramps defined into top and bottom surfaces of the front plate, and the front ramp may include a pair of male horizontal ramps configured to interface with the female horizontal ramps of the front plate. The horizontal ramps of the front plate may be slanted such that one end of each ramp starts at a side of the front plate and extends toward a center of the front plate with the horizontal ramps leading toward one another. One of the female horizontal ramps may have a depth greater than the other female horizontal ramp.

According to another embodiment, an expandable intervertebral implant includes front and rear plates, a central drive screw, and left and right side portion assemblies. The front plate has at least one ramp and the rear plate has at least one ramp. The central drive screw is threadedly engaged with a drive sleeve. The central drive screw is retained in the rear plate and the drive sleeve retained in the front plate. The left and right side portion assemblies each include an upper endplate, a lower endplate, an actuator, and a front ramp. The actuator includes a ramp slidably engaged with the ramp of the rear plate, and the front ramp includes a ramp slidably engaged with the ramp of the front plate. Rotation of the drive screw moves the front plate toward the rear plate and the ramp of the actuator slides across the ramp of the rear plate, and the ramp of the front ramp slides across the ramp of the front plate, thereby expanding a width of the implant.

The expandable implant may include one or more of the following attributes. The ramps of the front plate and the rear plate may include horizontal ramps aligned along one or more horizontal planes. The rear plate may include a pair of female ramps defined into top and bottom surfaces of the rear plate, and the actuator may include a pair of male ramps configured to interface with the female ramps of the rear plate. The front plate may include a pair of female ramps defined into top and bottom surfaces of the front plate, and the front ramp may include a pair of male ramps configured to interface with the female ramps of the front plate. The left and right side portion assemblies may have a laterally collapsed configuration having a first width and a laterally expanded configuration having a second width. The left and right side portion assemblies may have a vertically collapsed configuration having a first height and a vertically expanded configuration having a second height. Rotation of the drive screw moves the front plate toward the rear plate, thereby first transitioning the left and right side portion assemblies to the laterally expanded configuration and then to the vertically expanded configuration. The drive sleeve may include a tubular body with an internally threaded bore, and the central drive screw may include an externally threaded shaft allowing for threaded engagement with the internally threaded bore of the drive sleeve. A distal end of the drive sleeve may include an exterior threaded portion receivable through a bore defined through the front plate and a lock nut may be coupled to the threaded portion of the drive sleeve, thereby securing the drive sleeve to the front plate. The drive sleeve may include a pair of keys on an outer surface of the drive sleeve configured to mate with a pair of keyways in the bore of the front plate, thereby preventing the drive sleeve from rotating.

According to another embodiment, an expandable intervertebral implant includes front and rear plates each having horizontal and vertical ramps, a central drive screw for moving the front plate relative to the rear plate, an expandable assembly, and a stationary assembly. The expandable assembly includes an upper endplate, a lower endplate, an actuator, and a front ramp. The upper and lower endplates include vertical ramps. The actuator includes horizontal ramps interfacing with the horizontal ramps of the rear plate and vertical ramps interfacing with the vertical ramps of the upper and lower endplates. The front ramp has horizontal ramps interfacing with the horizontal ramps of the front plate and vertical ramps interfacing with the vertical ramps of the upper and lower endplates. The stationary assembly includes upper and lower endplates having vertical ramps interfacing with the vertical ramps of the front and rear plates. Rotation of the drive screw moves the front plate toward the rear plate, thereby expanding the expandable assembly in width and then expanding both the expandable and stationary assemblies in height.

The expandable implant may include one or more of the following attributes. The front and rear plates may include only a single horizontal ramp on top and bottom faces of the plates to engage with a single actuator and front ramp of the expandable assembly, respectively. The front and rear plates may each include a female horizontal ramp configured to interface with male horizontal ramps of the actuator and front ramp of the expandable assembly, respectively. The upper and lower endplates of the expandable assembly may define female vertical ramps configured to interface with male vertical ramps of the actuator and front ramp, respectively.

According to another embodiment, an expandable intervertebral implant includes front and rear plates, a central drive screw threadedly engaged with a drive sleeve, the central drive screw retained in the rear plate and the drive sleeve retained in the front plate, left and right side portion assemblies each including upper and lower endplates, an actuator, and a front ramp, and an endplate clip positioned around the drive sleeve to prevent expansion of the upper and lower endplates in height until the left and right side portion assemblies are fully expanded in width.

The expandable implant may include one or more of the following attributes. When the drive screw is rotated, the implant expands in width and once the upper and lower endplates are released from the endplate clip, then the implant expands in height. The endplate clip may include a ring with a plurality of posts configured to engage the upper and lower endplates. The ring may include a full ring defining a central bore sized and dimensioned to snuggly fit around the drive sleeve. The posts may extend from the ring and terminate at one or more free ends. Before the implant is fully expanded, the free ends of the posts are receivable in bores through a side wall of the endplates, thereby preventing any expansion in height. Once fully expanded in width, the endplates move outward and away from one another and the free ends of the posts are released from the bores, thereby allowing the upper and lower endplates to expand in height. A first post may be positioned above the ring with two opposed free ends extending into the upper endplates, respectively, and a second post may be positioned below the ring with two opposed free ends extending into the lower endplates, respectively. The two posts may be aligned in parallel.

According to another embodiment, an expandable intervertebral implant includes a front plate having at least one ramp and a rear plate having at least one ramp. A central drive screw threadedly engaged with a drive sleeve. The central drive screw retained in the rear plate and the drive sleeve retained in the front plate. Left and right side portion assemblies each including an upper endplate, a lower endplate, an actuator, and a front ramp. The actuator includes a ramp slidably engaged with the ramp of the rear plate, and the front ramp includes a ramp slidably engaged with the ramp of the front plate. An endplate clip is positioned between the drive sleeve and the upper and lower endplates. Rotation of the drive screw moves the front plate toward the rear plate and the ramp of the actuator slides across the ramp of the rear plate, the ramp of the front ramp slides across the ramp of the front plate, thereby expanding a width of the implant. The endplate clip prevents expansion of the upper and lower endplates in height until the left and right side portion assemblies are fully expanded in width.

The expandable implant may include one or more of the following attributes. The drive sleeve may include a tubular body with an internally threaded bore, and the central drive screw may include an externally threaded shaft allowing for threaded engagement with the internally threaded bore of the drive sleeve. The endplate clip may include a ring fitted over the tubular body of the drive sleeve with a plurality of outwardly extending posts configured to engage the upper and lower endplates. The endplate clip may include a first post affixed to a top of the ring and a second post affixed to a bottom of the ring. The first post may terminate at first and second free ends configured to engage the upper endplates and the second post may terminate at third and fourth free ends configured to engage the lower endplates. The first and second posts may be horizontally aligned with the upper and lower endplates, respectively. Before the implant is fully expanded, the free ends of the posts may be receivable in bores through a side wall of the endplates, thereby preventing any expansion in height.

According to another embodiment, an expandable intervertebral implant includes front and rear plates each having horizontal ramps, a central drive screw for moving the front plate relative to the rear plate, an expandable assembly including an upper endplate, a lower endplate, an actuator, and a front ramp, wherein the upper and lower endplates include vertical ramps, the actuator includes horizontal ramps engaged with the horizontal ramps of the rear plate and vertical ramps engaged with the vertical ramps of the upper and lower endplates, and the front ramp having horizontal ramps engaged with the horizontal ramps of the front plate and vertical ramps interfacing with the vertical ramps of the upper and lower endplates, and an endplate clip attached to the drive sleeve to prevent expansion of the upper and lower endplates in height until the expandable assembly is fully expanded in width.

The expandable implant may include one or more of the following attributes. The endplate clip may include one or more posts receivable in corresponding bores in the upper and lower endplates. The endplate clip only permits lateral expansion of the expandable assembly until the posts disengage from the bores in the upper and lower endplates. A first post is receivable in the bore in the upper endplate and a second post is receivable in the bore in the lower endplate, and the first and second posts may be aligned in parallel.

According to another embodiment, a method of assembling an expandable implant includes, in any suitable order: (1) placing two front ramps onto a front plate by aligning the ramp/sliding features of the two components; (2) placing two actuators onto a rear plate by aligning the ramp/sliding features of the two components; (3) assembling each of the left and right side assemblies by (a) placing lower and upper endplates onto the actuator and placing a front ramp into both the lower and upper endplates or (b) placing the upper endplate onto the actuator and placing the front ramp onto the upper endplate, then placing the lower endplate onto both the actuator and the front ramp while ensuring all ramps are engaged with one another; (4) inserting a threaded drive sleeve into the front plate and securing with a lock nut; (5) securing an endplate clip to the threaded sleeve and engaging posts of the endplate clip into bores in the endplates; (6) assembling a friction ring onto the drive screw and inserting the drive screw through the rear plate; (7) threading the drive screw into the drive sleeve; and (8) securing the drive screw to the rear plate with a lock ring.

According to yet another embodiment, a kit may include a plurality of implants of different sizes and configurations. The kit may further include one or more devices suitable for installing and/or removing the assemblies described herein, such as insertion devices or drivers; one or more removal devices; and other tools and devices, which may be suitable for surgery.

BRIEF DESCRIPTION OF THE DRAWINGS

The present embodiments will become more fully understood from the detailed description and the accompanying drawings, wherein.

DETAILED DESCRIPTION

Embodiments of the disclosure are generally directed to devices, systems, and methods for intervertebral fusion. Specifically, expandable implants are configured to increase the overall footprint size after being inserted into the disc space while also adjusting the lordosis and overall height. The expandable implants may include one or more side assemblies configured to expand in width and in height. In doing so, the expansion addresses sagittal balance correction and subsidence issues.

A spinal fusion is typically employed to eliminate pain caused by the motion of degenerated disc material. Upon successful fusion, a fusion device becomes permanently fixed within the intervertebral disc space. The expandable fusion device may be positioned between adjacent vertebral bodies in a collapsed position. The expandable fusion device is configured to expand in width and subsequently in height. The fusion device engages the endplates of the adjacent vertebral bodies and, in the installed position, maintains desired intervertebral disc spacing and restores spinal stability, thereby facilitating an intervertebral fusion.

Minimally invasive surgery (MIS) may be used to preserve muscular anatomy by only causing disruption where necessary. The benefit of the MIS surgical approach is that it can reduce post-operative pain and improve recovery time for patients. In one embodiment, the expandable fusion device can be configured to be placed down an endoscopic tube and into the surgical target site. By way of example, the surgical site may be an intervertebral disc space situated between two adjacent vertebrae. Although particularly suited for use in a transforaminal lumbar interbody fusion (TLIF), it will be readily appreciated by those skilled in the art that the implant may be employed in any number of suitable orthopedic approaches and procedures, including but not limited to, anterior, posterior, lateral, anterolateral, or posterolateral approaches to the lumbar spine, cervical spine, or thoracic spine, as well as any non-spine application, such as treatment of bone fractures and the like.

Components of all of the devices disclosed herein may be manufactured of any suitable materials including metals (e.g., titanium), metal alloys (e.g., stainless steel, cobalt-chromium, and titanium alloys), ceramics, plastics, plastic composites, or polymeric materials (e.g., polyether ether ketone (PEEK), polyphenylene sulfone (PPSU), polysulfone (PSU), polycarbonate (PC), polyetherimide (PEI), polypropylene (PP), polyacetals, or mixtures or co-polymers thereof), and/or combinations thereof. In some embodiments, the devices may include radiolucent and/or radiopaque materials. The components can also be machined and/or manufactured using any suitable techniques (e.g., 3D printing).

Figure 1A:
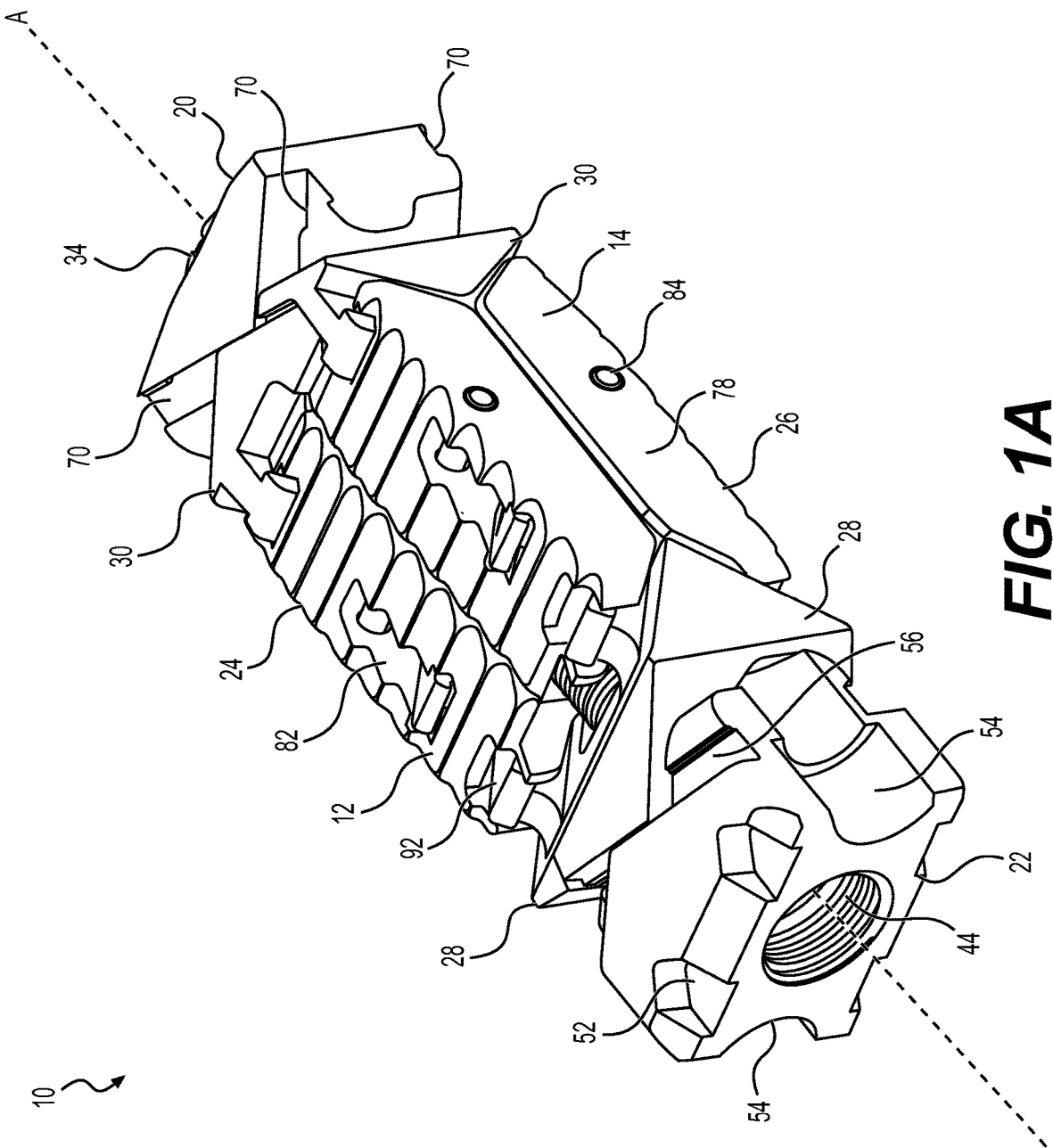
FIGS. 1A-1C illustrate perspective views of an expandable implant in a collapsed position, expanded in width, and expanded in width and height, respectively, according to one embodiment.
Figure 1B:
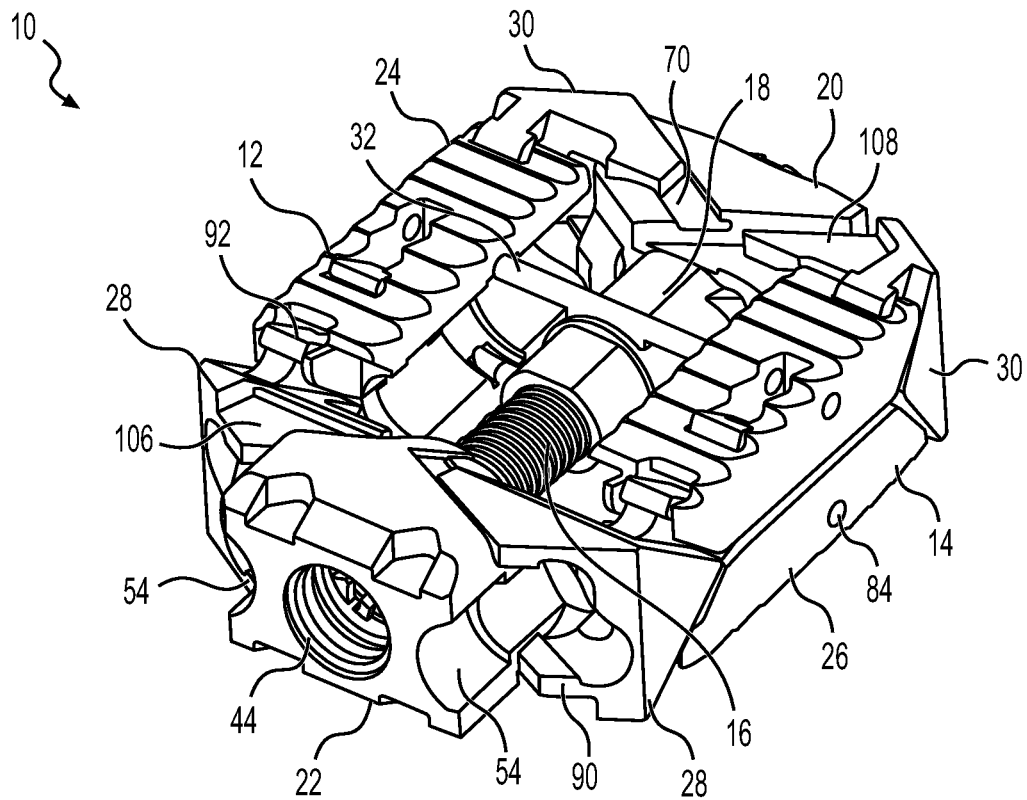
Figure 1C:
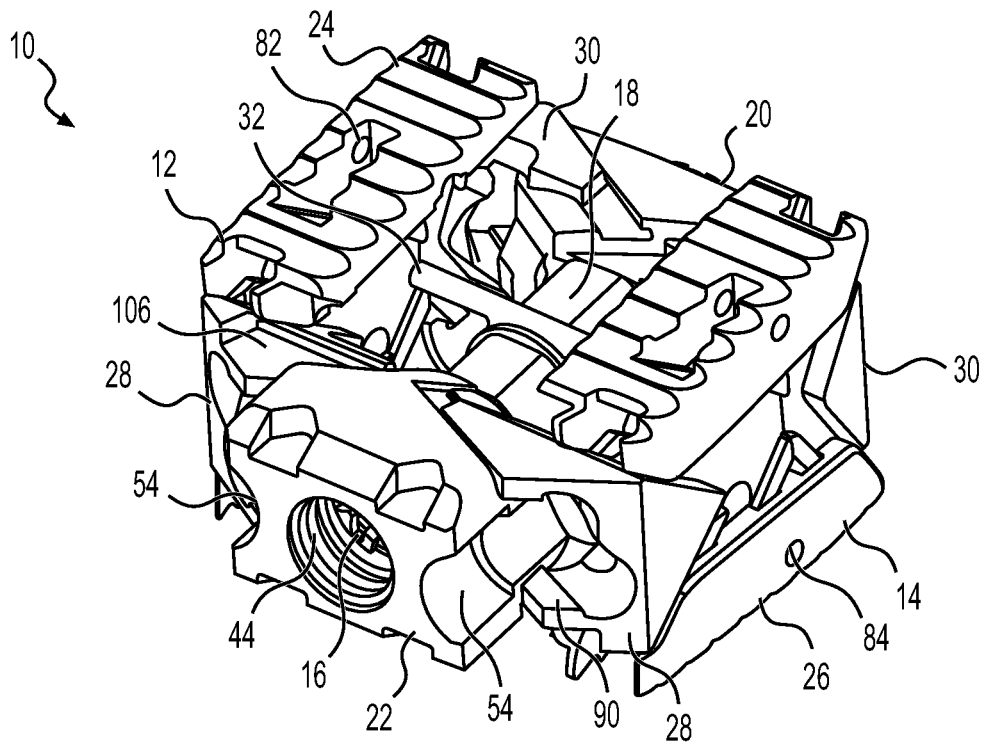

Turning now to the drawing, where like reference numerals refer to like elements, FIGS. 1A-1C illustrate an expandable fusion device or implant 10 according to one embodiment. The expandable fusion device 10 may include left and right side portion assemblies 12, 14 configured to expand in width to increase the overall footprint of the device 10 and expand in height to correct disc height restoration, lordosis, and/or sagittal balance. The implant 10 may be suitable for a transforaminal lumbar interbody fusion (TLIF) through a posterior approach or other suitable surgical procedure.

The expandable fusion device 10 extends along a central longitudinal axis A between front and rear ends of the device 10. FIG. 1A shows the expandable fusion device 10 in a fully collapsed configuration with the left and right side portions 12, 14 collapsed in both width and height. FIG. 1B shows the expandable fusion device 10 in an expanded configuration with the left and right side portions 12, 14 expanded in width. FIG. 1C shows the expandable fusion device in a fully expanded configuration with the left and right side portions 12, 14 expanded in width and in height. It should be understood that references to the front and rear ends and left and right side portions 12, 14 are described with respect to the direction of placement into an intervertebral disc space with the front of the expandable fusion device 10 placed into the disc space first, followed by the rear of the expandable fusion device 10. These and other directional terms may be used herein for descriptive purposes and do not limit the orientation(s) in which the devices may be used.

Figure 2:
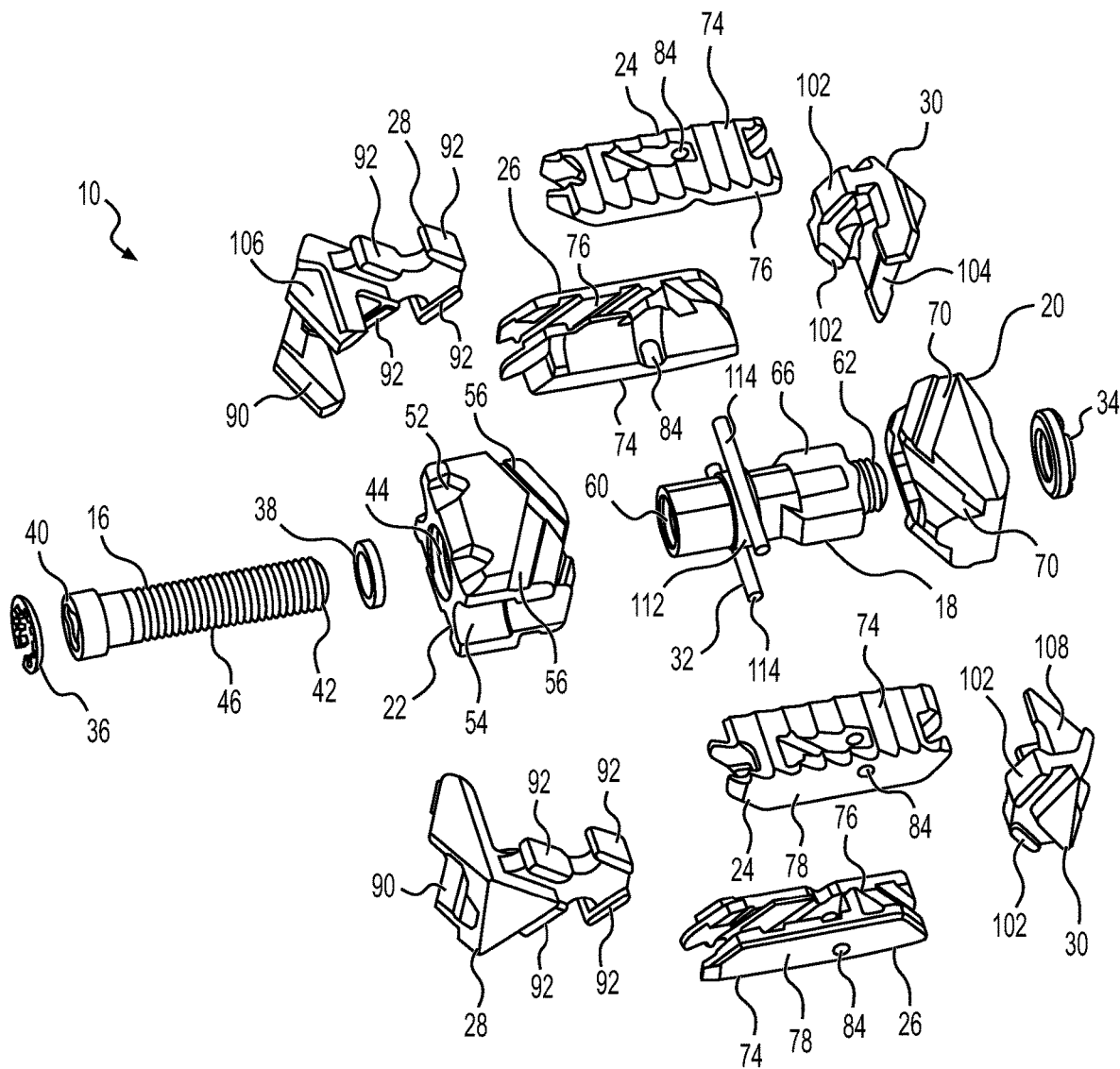
FIG. 2 shows an exploded view of the expandable implant of FIGS. 1A-1C.

With emphasis on the exploded view in FIG. 2, movement of the first half or left side portion 12 and the second half or right side portion 14 of the implant 10 is controllable by a central drive screw 16 which is attached to a front distal plate 20 and rear proximal plate 22. The drive screw 16 pulls the distal plate 20 towards the proximal plate 22 and pushes the left and right portions 12, 14 outwards via horizontal ramps or slides 56, 70, 90, 104.

The central drive screw 16 is positioned into and threadedly engaged with a central drive sleeve 18. The central drive screw 16 and central drive sleeve 18 may be positioned along the central longitudinal axis A of the device 10. The central drive sleeve 18 is attached to the front distal block or plate 20 and the central drive screw 16 is attached to a rear proximal block or plate 22. For example, the central drive sleeve 18 may be attached to the front distal plate 20 with a lock nut 34 and the central drive screw 16 may be retained within the rear proximal plate 22 with a locking ring or retaining ring 36. The drive screw 16 is configured to pull the front distal plate 20 towards the rear proximal plate 22, thereby pushing the left and right side portions 12, 14 outwards and away from one another via the mating horizontal ramps 56, 70, 90, 104 along the front and rear plates 20, 22, the actuators 28, and the front ramps 30, respectively.

Once the left and right side portion assemblies 12, 14 are fully expanded in width, the distal plate 20 may continue to travel to allow for vertical expansion of the left and right side portions 12, 14, thereby increasing the height of the device 10. For example, the left and right side portion assemblies 12, 14 may each include upper and lower endplates 24, 26, an actuator 28, and a front ramp 30. Both of the front ramps 30 are actuated when the central drive screw 16 is turned. Rotation of the drive screw 16 pulls the front ramps 30 toward the actuators 28, which then expands the top and bottom endplates 24, 26 via mating vertical ramps 80, 92, 102 between the endplates 24, 26, the actuators 28, and the front ramps 30, respectively.

Figure 3:
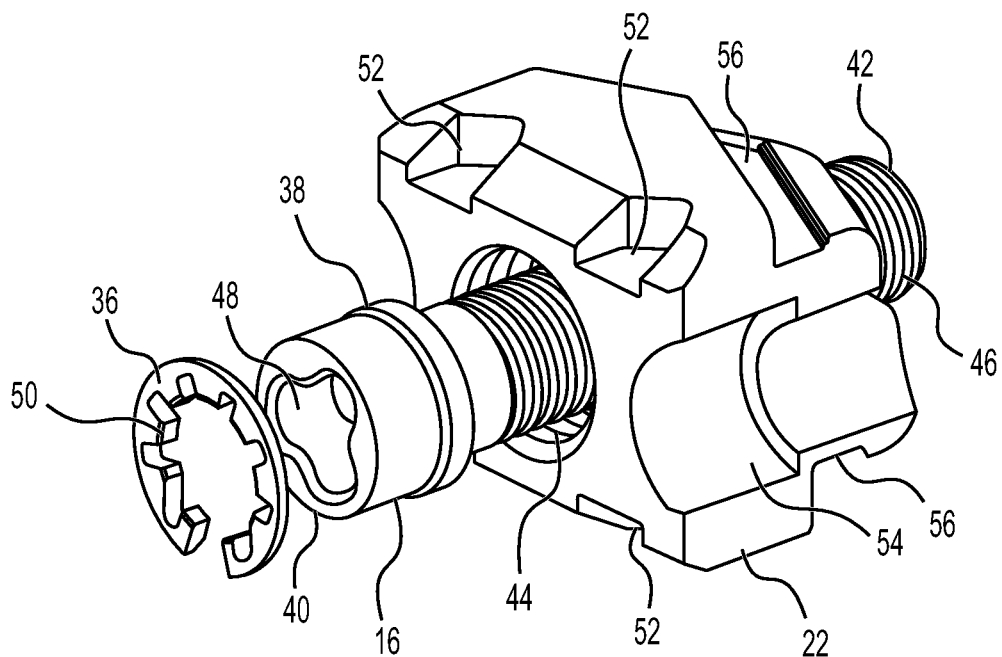
FIG. 3 show an exploded view of a retaining ring positionable on the drive shaft of the expandable implant to secure the drive shaft to the rear plate according to one embodiment.

As best seen in FIG. 3, the drive screw 16 extends from a proximal end 40 to a distal end 42. The proximal end 40 may include an enlarged head portion configured to be received in a bore 44 defined through the rear proximal plate 22. The bore 44 in the rear plate 22 may be internally threaded to provide for a threaded connection to the rear plate 22, for example, allowing for a rigid connection to an insertion instrument. The proximal end 40 of the drive screw 22 may define an instrument recess 48 configured to receive an instrument, such as a driver, to rotate or actuate the drive screw 16. The instrument recess 48 may include a tri-lobe, hex, star, or other suitable recess configured to engage with a driver instrument to apply torque to the drive screw 16. The drive screw 16 may include a shaft with an exterior threaded portion 46 extending along its length. The drive screw 16 is receivable through the bore 44 in the rear plate 22 such that the enlarged proximal head portion 40 of the drive screw 16 is receivable in the rear plate 22. An optional friction ring 38, such as a polyether ether ketone (PEEK) ring, may be assembled onto the drive screw 16, for example, below the enlarged head, to increase friction or drag on the drive screw 16 during rotation.

The central drive screw 16 may be retained within the rear proximal plate 22 with retaining ring 36. For example, the retaining ring 36 may include a split ring with a plurality of inner teeth 50 or various reliefs to allow the retaining ring 36 to compress and enter the bore 44 of the rear plate 22 and engage an internal groove in the plate 22. The retaining ring 36 may include two slots, for example, to be engaged with an instrument to aid insertion and removal of the retaining ring 36. When the retaining ring 36 is positioned around the drive screw 16 and within the bore 44 in the rear plate 22, the teeth 50 are configured to engage with the central drive screw 16, thereby locking the screw 16 in position in the plate 22.

The rear plate 22 may include one or more instrument slots 52 configured to be engaged by an instrument, such as an insertion instrument. For example, the top and bottom faces of the rear plate 22 may each include a pair of instrument slots 52. The rear plate 22 may also define one or more side recesses 54 configured to receive a graft delivery device. For example, opposite sides of the rear plate 22 may include two opposed semi-circular recesses 54 configured to allow the graft delivery device to enter the central portion of the implant 10 once fully expanded in width and/or height. Bone graft or similar bone growth inducing material can be introduced within and/or around the fusion device 10 to further promote and facilitate the intervertebral fusion.

The rear plate 22 includes one or more ramps 56 configured to interface with corresponding ramps 90 on the actuators 28 of the left and right side portions 12, 14. For example, near the distal end of the rear plate 22, the rear plate 22 may include a pair of ramps 56 defined into each of the top and bottom surfaces of the rear plate 22. The ramps 56 may be horizontal ramps aligned along one or more horizontal planes. For example, one of the pair of ramps 56 may be positioned along one given horizontal plane lower or higher relative to the other ramp 56 along another given horizontal plane. In other words, each ramp 56 has a constant depth along its length such that one ramp 56 has a depth greater than the other ramp 56. The horizontal ramps 56 may be angled, diagonal, or slanted such that one end of the ramp 56 starts at a side of the rear plate 22 and extends toward the center back of the rear plate 22 with the ramps 56 leading toward one another. The horizontal ramps 56 may define female channels or grooves configured to receive the mating male counterparts 90 of the actuators 28. It will be appreciated, however, that the female/male configurations may be reversed or may include other suitable ramp interactions, sliding features, or mating components to provide lateral expansion of the left and ride side portions 12, 14.

Figure 5:
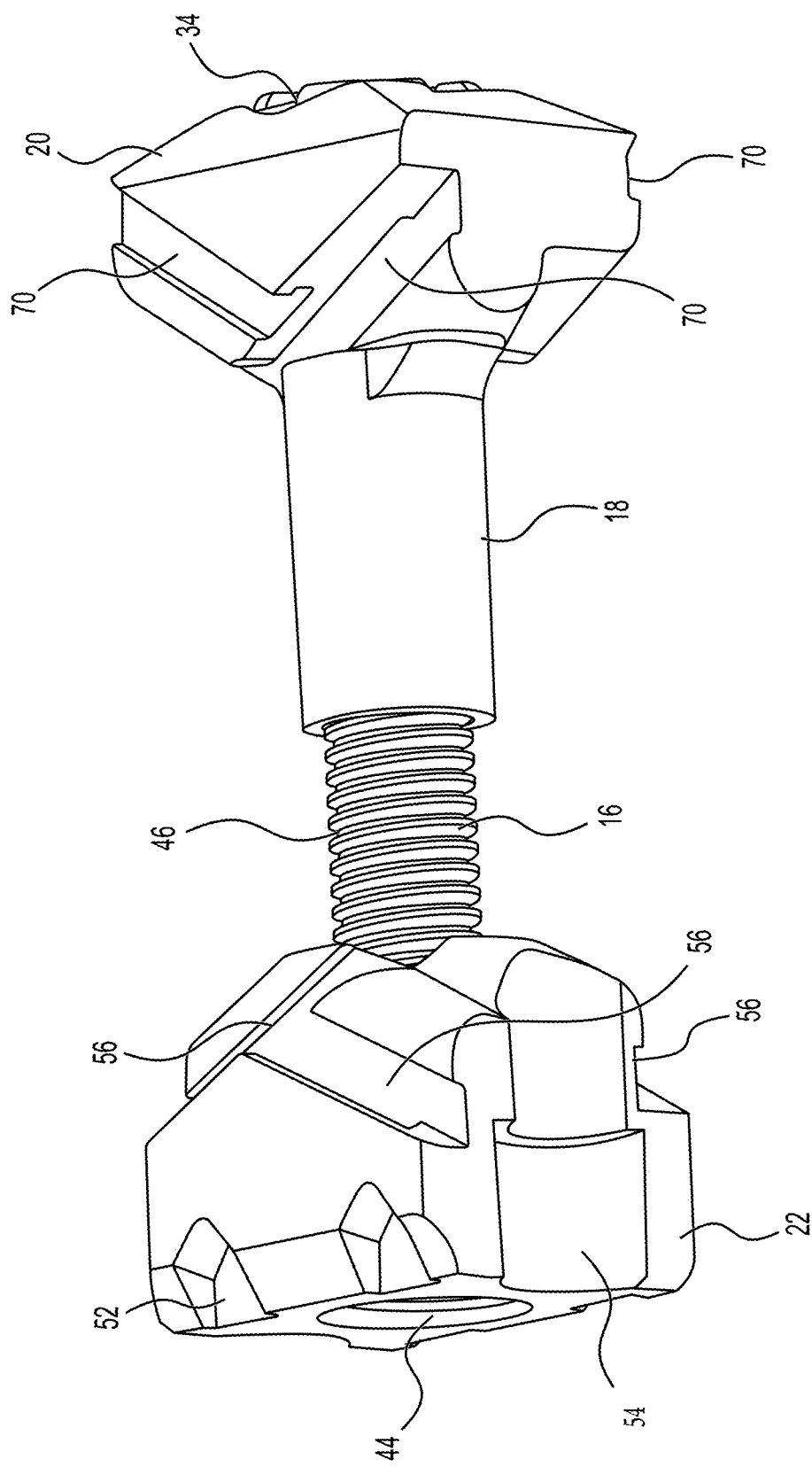
FIG. 5 shows the rear plate attached to the drive screw, the drive sleeve attached to the front plate, and the drive screw threadedly engaged to the drive sleeve of the expandable implant according to one embodiment.

As best seen in FIGS. 5, the threaded shaft 46 of the drive screw 16 may be receivable through the body of the drive sleeve 18. The drive sleeve 18 may have a tubular body with an inner bore 60 that is internally threaded to allow for threaded engagement with the threaded shaft 46 of the drive screw 16. As the drive screw 16 is threaded into the drive sleeve 18, actuation of the drive screw 16 is configured to push or pull the front plate 20. When the front plate 20 is pulled toward the rear plate 22, the implant 10 expands in width and then height once fully assembled.

The drive sleeve 18 may have an exterior threaded portion 62 at its distal end. The distal threaded portion 62 may fit into an opening 64 defined through the front distal plate 20. After being positioned through the bore 64 in the front plate 20, the drive sleeve 18 may be secured to the front distal plate 20 with the lock nut 34. The lock nut 34 may include a ring with a central bore defining internal threads. The drive sleeve 18 may be secured to the front distal plate 20 by coupling the internally threaded lock nut 34 to the distal threaded portion 62 of the drive sleeve 18. An outward face of the lock nut 34 may include one or more instrument recesses for engagement with an instrument to rotate the lock nut 34.

Figure 4:
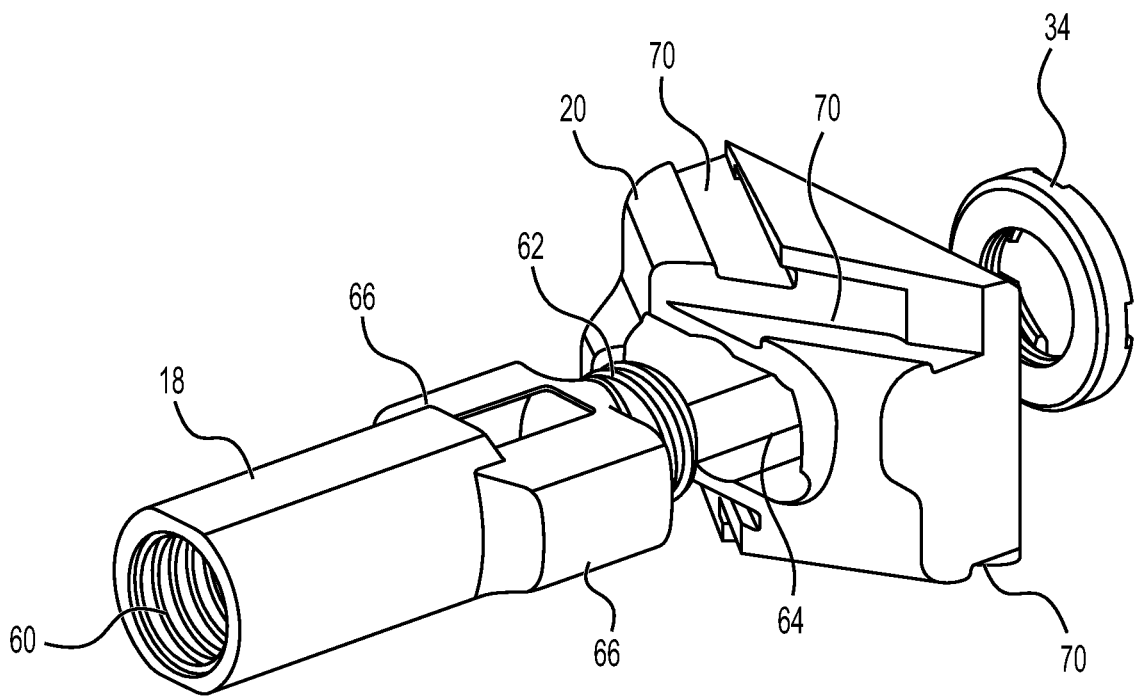
FIG. 4 shows an exploded view of a drive sleeve insertable into the front plate and configured to be retained by a lock nut according to one embodiment.

With emphasis on FIG. 4, the drive sleeve 18 may be keyed to the opening 64 through the front plate 20 with one or more keying portions 66 configured to ensure the orientation of the drive sleeve 18 relative to the front plate 20. For example, the keying portions 66 may include a pair of opposite wings on an outer surface of the sleeve 18 configured to mate with a corresponding keyway through the opening 64. The wings 66 may extend between upper and lower portions of the sleeve 18 and may have a central vertical opening therebetween. The wings 66 may include planar surfaces, curved surfaces, or other suitable surfaces configured to mate with the corresponding opening 64. It will be appreciated that any suitable number, type, or configuration of keying portions 66 may be selected to align the sleeve 18 with the front plate 20. For example, the keying portions 66 may include a dovetail interface, finger joint, pin(s), or other suitable keying feature(s) to ensure the desired orientation. The keying portions 66 and opening 64 are aligned to lock the sleeve 18 from rotation. When the drive screw 16 is rotated or actuated, the drive sleeve 18 and attached front plate 20 are drawn toward the rear plate 22, thereby providing for expansion of the device 10.

The front plate 20 includes one or more ramps 70 configured to interface with corresponding ramps 104 on the front ramps 30 of the left and right side portions 12, 14. Similar to ramps 56, ramps 70 may include horizontal ramps defining female channels or grooves configured to receive the mating male counterparts 104 of the front ramps 30. It will be appreciated, however, that the female/male configurations may be reversed or may include other suitable ramp interactions, sliding features, or mating components to provide lateral expansion of the left and ride side portions 12, 14. In one embodiment, the front plate 20 may include a first pair of horizontal ramps 70 defined into the top of the front plate 20 and a second pair of horizontal ramps 70 defined into the bottom of the front plate 20. Each of the ramps 70 may be aligned along distinct horizontal planes. In this manner, each ramp 70 has a constant depth along its length such that one of the female horizontal ramps has a depth greater than the other female horizontal ramp. For example, a first ramp 70 defined along the top of the front plate 20 may be positioned along one given horizontal plane lower or higher relative to the other ramp 70 defined along the top of the front plate 20. The horizontal ramps 70 may be angled, diagonal, or slanted such that one end of each ramp 70 begins at a side of the front plate 20 and extend centrally in a direction towards the drive sleeve 18 with the ramps 70 leading toward one another.

Figure 6:
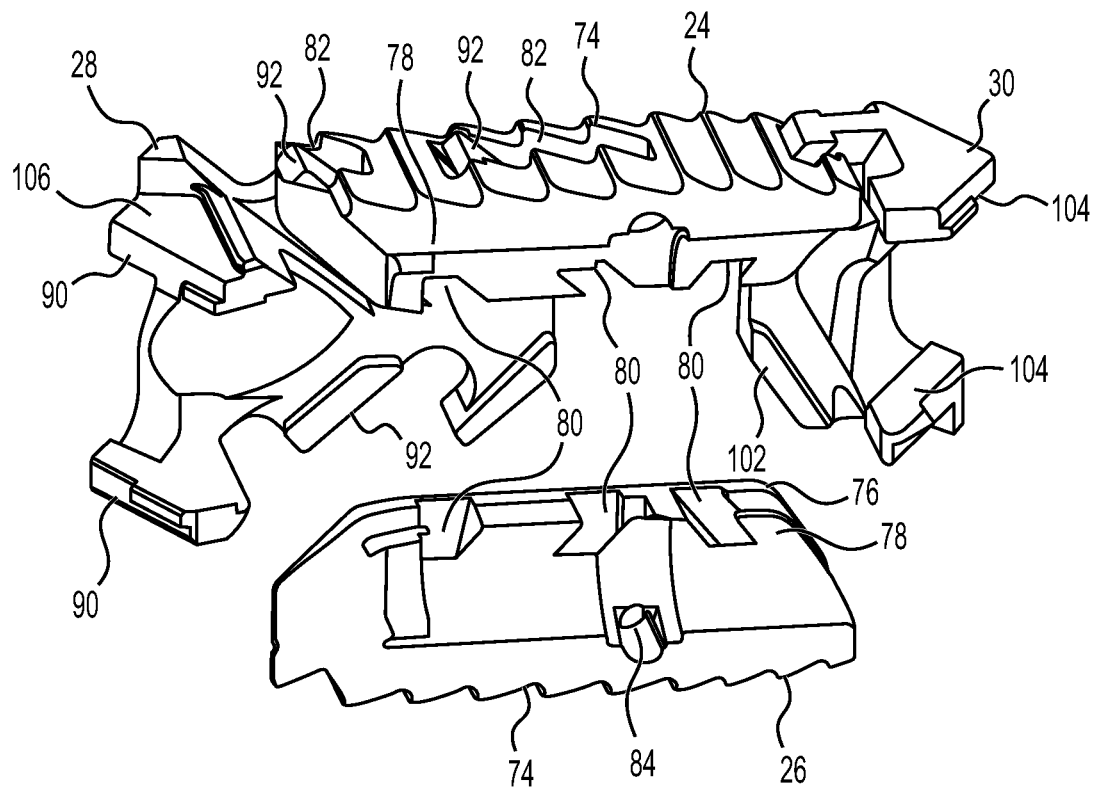
FIG. 6 shows the top endplate assembled onto the actuator and the front ramp and a lower endplate configured to be placed onto the actuator and front ramp during assembly.
Figure 7:
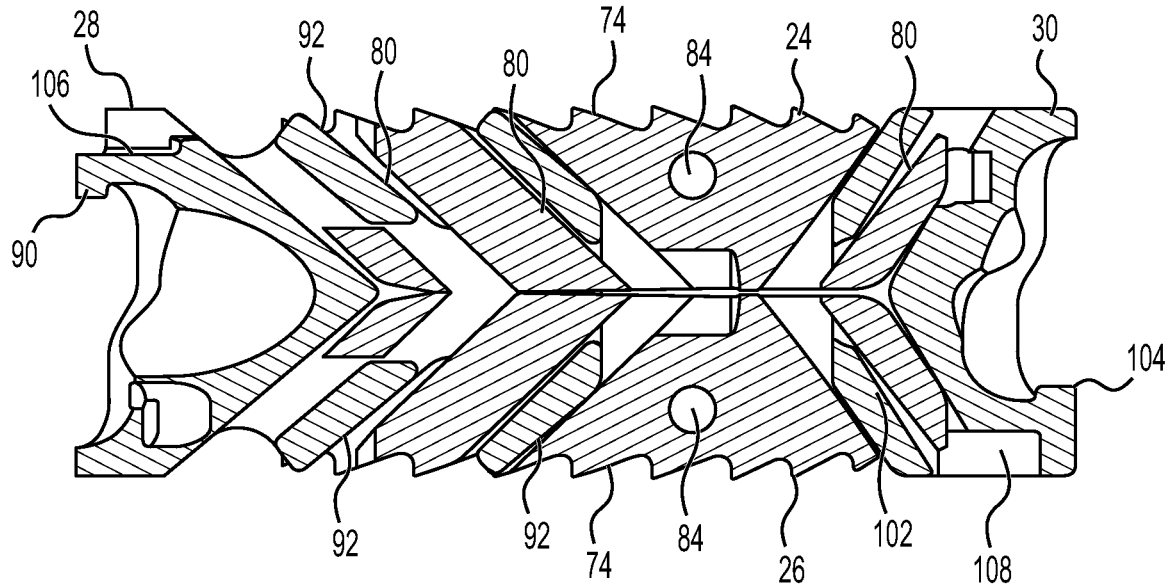
FIG. 7 shows a cross-sectional view of the ramps of the upper and lower endplates engaged with the actuator and front ramp according to one embodiment.

With emphasis on FIGS. 6 and 7, the left and right side portion assemblies 12, 14 may each include upper and lower endplates 24, 26 configured to expand away from one another to increase the vertical height of the expandable fusion device 10. The upper and lower endplates 24, 26 may be the same or mirror images of one another. Although described with reference to the upper endplate 24, the discussion herein applies equally to the lower endplate 26. The upper endplate 24 includes an upper or outer facing surface 74 configured to interface with the vertebral endplate (s) of the adjacent vertebral bodies when implanted in the disc space. The outer surface 74 may include a plurality of teeth, ridges, roughened surfaces, keels, gripping or purchasing projections, or other friction increasing elements configured to retain the device 10 in the disc space. For example, the endplates 24, 26 may be 3D printed using additive manufacturing to provide a natural roughened surface to promote boney on growth or may be machined and blasted to achieve a roughened surface.

The upper endplate 24 includes a lower or inner facing surface 76 and one or more side walls 78 defining one or more ramps 80 configured to interface with corresponding ramps 92 on the actuator 28 and front ramp 30. For example, the upper endplate 24 may define at least three ramps 80 along the inner side wall 78 of the endplate 24. The ramps 80 may be vertical ramps aligned along one or more vertical planes. In one embodiment, all three vertical ramps 80 may be aligned along the same plane. Although vertically-oriented, the vertical ramps 80 may be angled, diagonal, or sloped to increase the vertical height of the endplates 24, 26. In one embodiment, two vertical ramps 80 interfaced with the actuator 28 may be angled in one direction and a third vertical ramp 80 interfaced with the front ramp 30 may be angled in an opposite direction. For example, the distal-most vertical ramp 80, near front ramp 30, may be sloped such that it points toward the front ramp 30 as it extends along the side wall 78 from the inner surface 76 toward the outer surface 74. Similarly, the proximal-most vertical ramp 80, near the actuator 28, and centrally located vertical ramp 80, may be sloped such that they point toward the actuator 28 as they extend along the side wall 78 from the inner surface 76 toward the outer surface 74. The proximal-most vertical ramp 80 and central vertical ramp 80 may be aligned in parallel with the same degree of slope. The vertical ramps 80 may define female channels or grooves configured to receive the mating male counterparts 92, 102 of the actuator 28 and front ramp 30. It will be appreciated that the female/male configurations may be reversed or may include other suitable ramp interactions, sliding features, or mating components to provide vertical expansion of the left and ride side portions 12, 14.

One or more openings 82 may extend vertically through the body of the endplate 24. In the collapsed position, as shown in FIG. 1A, portions 92 of the actuators 28 may be received through the openings 82. Similarly, when expanded in width, as shown in FIG. 1B, the ramps 92 of the actuators 28 are receivable through the openings 82 in the endplates 24, 26. In the vertically expanded position, as shown in FIG. 1C, the openings 82 may be open and free to receive bone-graft or other suitable bone forming material. One or more openings or bores 84 may extend horizontally through the sidewalls 78 of the endplate 72, 74. The through bores 84 are configured to receive endplate clip 32 to prevent vertical expansion until horizontal expansion is complete.

Figure 8:
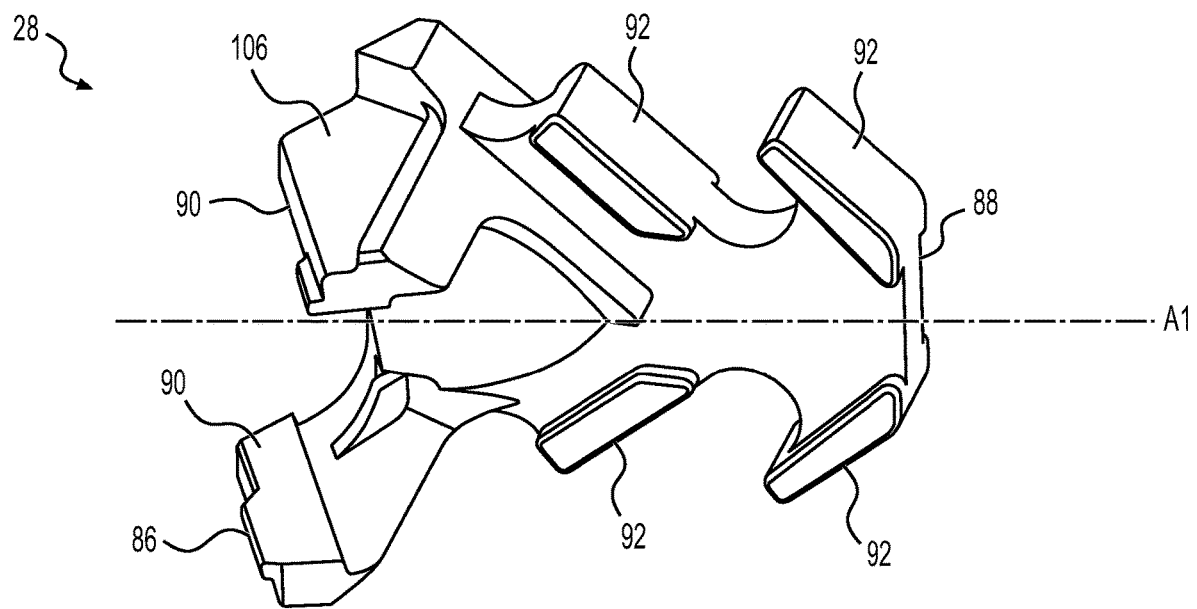
FIG. 8 shows the actuator of the side assemblies according to one embodiment.

The left and right side portion assemblies 12, 14 may include first and second actuators 28 positioned between the upper and lower endplates 24, 26 of the left and right side portions 12, 14, respectively. As best seen in FIG. 8, the actuator 28 may include a body extending along a central axis A1 from a proximal end 86 to a distal end 88. Central axis A1 may be generally parallel with central longitudinal axis A. The proximal end 86 may define one or more horizontal ramps 90 configured to engage with the horizontal ramps 56 of the rear plate 22. The actuator 28 may define a pair of top and bottom horizontal ramps 90 pointing inwardly toward one another. The horizontal ramps 90 may have an angled, diagonal, or slanted surface in a manner complimentary to the ramps 56 of the rear plate 22. In particular, the horizontal ramps 90 may define male projections configured to enter the female counterparts 56 of the rear plate 22.

The actuator 28 includes a plurality of ramps 92 configured to engage with the endplates 24, 26. The actuator 28 may define a plurality of vertical ramps 92 configured to engage with the vertical ramps 80 of the endplates 24, 26. The actuator 28 may define a first pair of vertical ramps 92 pointing upwardly toward the proximal end 86 or downwardly toward the distal end 88 and a second pair of vertical ramps 92 pointing upwardly toward the distal end 88 or downwardly toward the proximal end 86 of the actuator 28. The vertical ramps 92 may have an angled, diagonal, or sloped surface in a manner complimentary to the ramps 80 of the endplates 24, 26. In particular, the vertical ramps 92 may define male projections configured to enter the female counterparts 80 of the endplates 24, 26.

Figure 9:
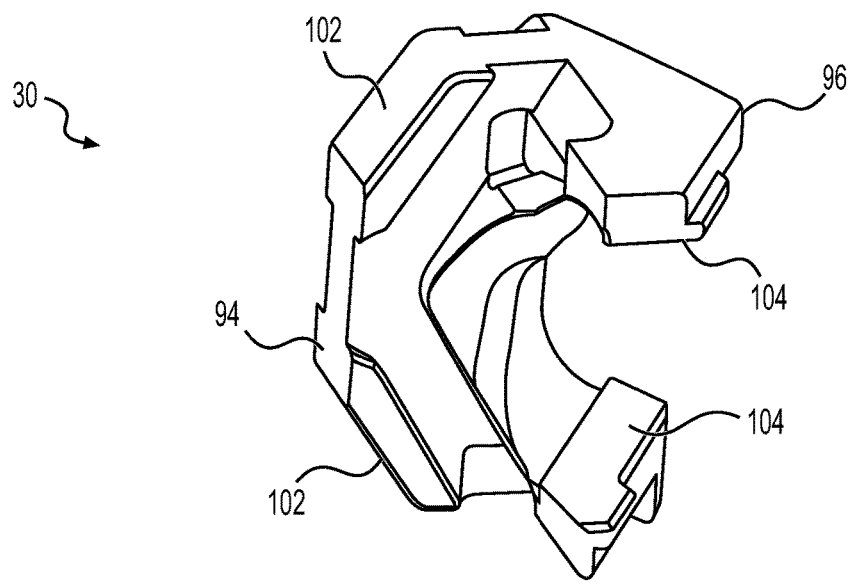
FIG. 9 shows the front ramp of the side assemblies according to one embodiment.

As shown in FIG. 9, the left and right side portions 12, 14 may each include front ramp 30 configured to expand the distal or front ends of the upper and lower endplates 24, 26. The front ramp 30 may include a body extending from a proximal end 94 to a distal end 96. The proximal end 94 may define one or more vertical ramps 102 configured to engage with the vertical ramps 80 of the endplates 24, 26. The front ramp 30 may define a first vertical ramp 102 pointing downwardly toward the proximal end 94 and a second vertical ramp 102 pointing upwardly toward the proximal end 94 of the front ramp 30. The vertical ramps 102 may have an angled, diagonal, or sloped surface in a manner complimentary to the ramps 80 of the endplates 24, 26. In particular, the vertical ramps 102 may define male projections configured to enter the female counterparts 80 of the endplates 24, 26.

The distal end 96 of the front ramp 30 may define one or more horizontal ramps 104 configured to engage with the horizontal ramps 70 of the front plate 20. The front ramp 30 may define a pair of top and bottom horizontal ramps 104 separated by a gap and pointing inwardly toward one another. The horizontal ramps 104 may have an angled, diagonal, or slanted surface in a manner complimentary to the ramps 70 of the front plate 20. In particular, the horizontal ramps 104 may define male projections configured to enter the female counterparts 70 of the front plate 20.

Figure 10A:
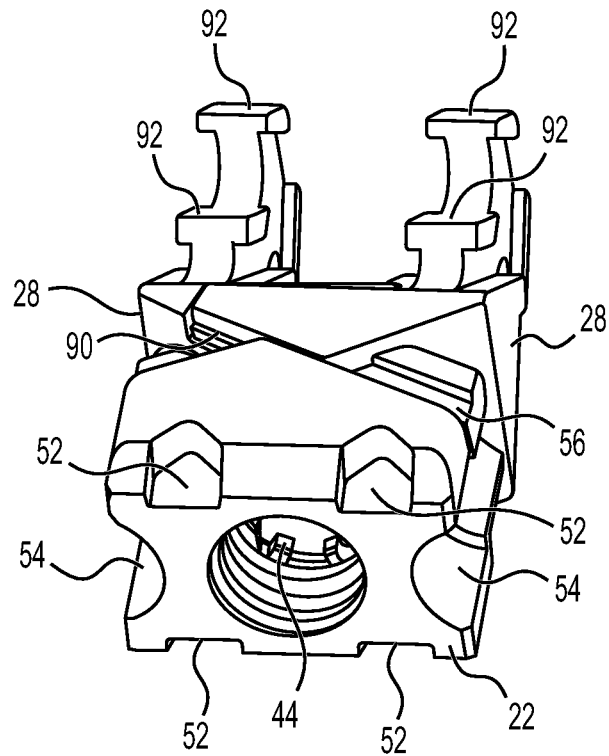
FIGS. 10A-10C illustrate the actuators slidably engaged with the rear plate in a collapsed position and expanded in width, respectively, and a close-up view of the interaction between the actuator and the rear plate according to one embodiment.
Figure 10B:
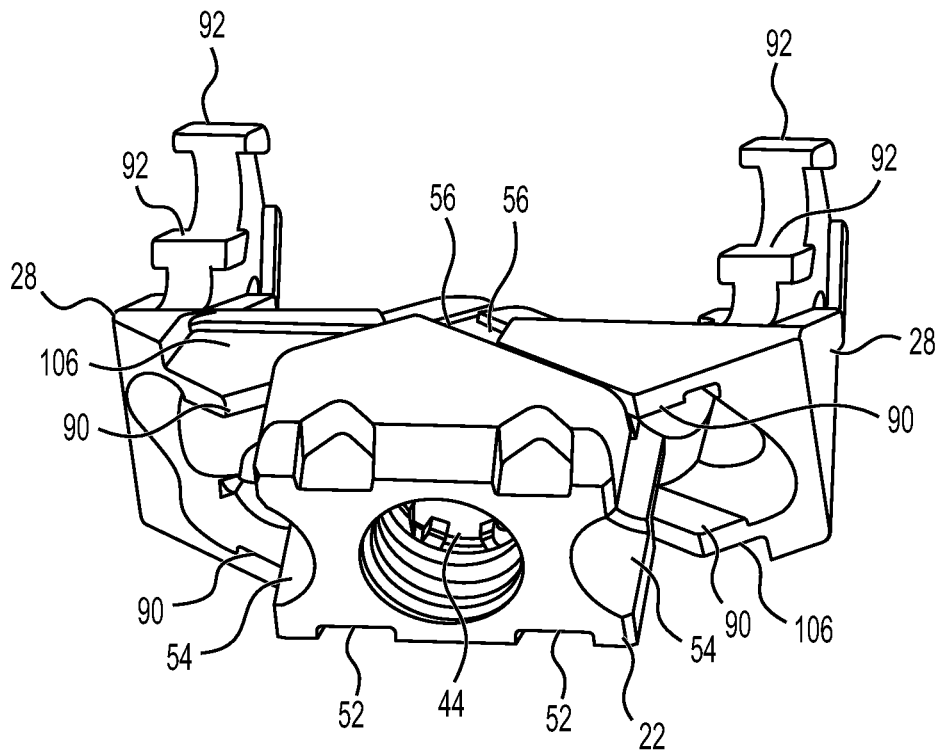
Figure 10C:
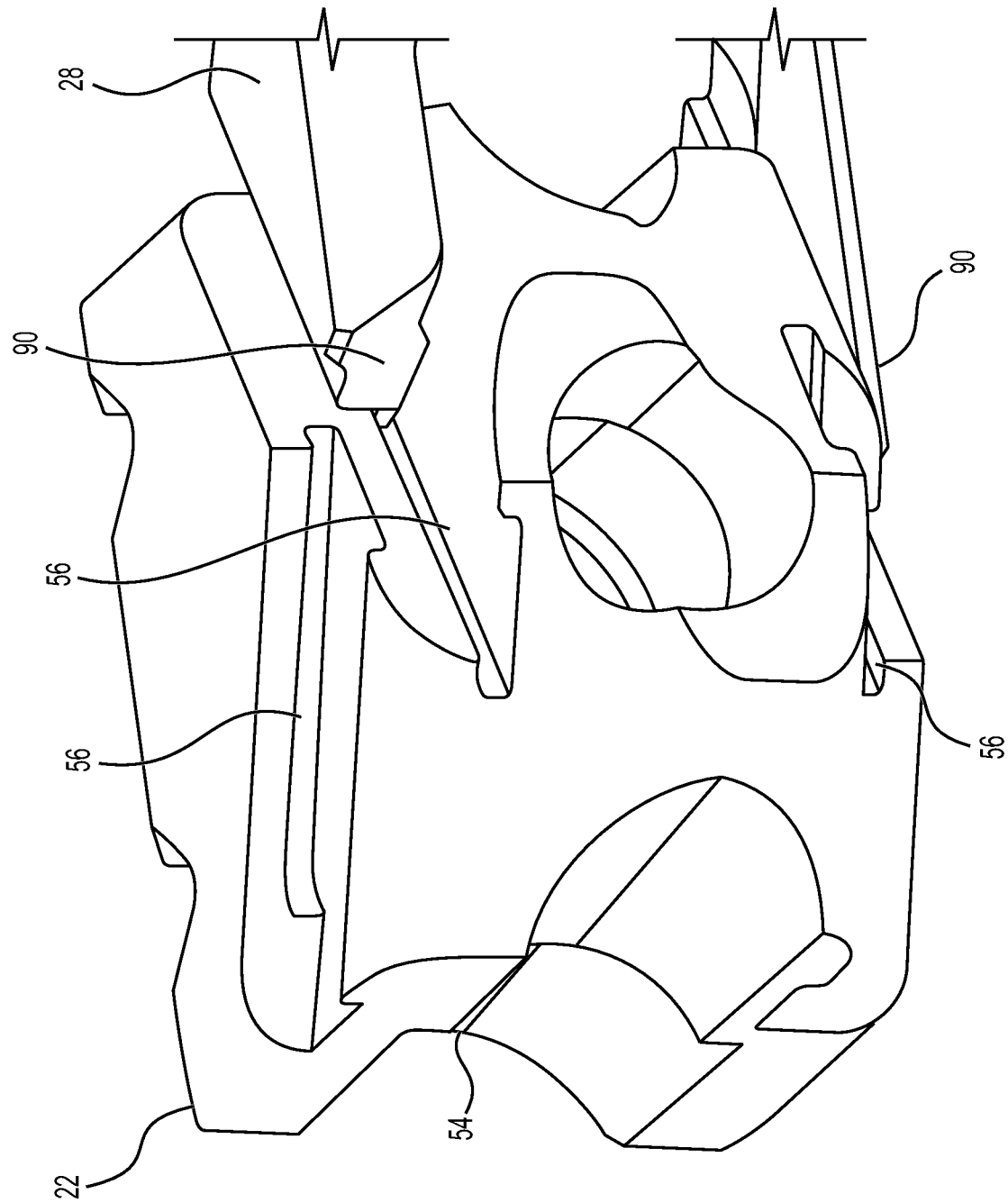

FIGS. 10A-10C show the actuators 28 slidably engaged with the rear plate 22 in collapsed and expanded positions, respectively. The actuators 29 slide onto the rear plate 22 by aligning keying features that control expansion. In FIG. 10A, the actuators 28 are engaged with the rear plate 22 and collapsed onto one another. A recessed surface 106 on top of one actuator 28 sized and dimensioned to receive the other actuator 28 permits the actuators 28 to nest together, thereby providing a small footprint for insertion. It will be appreciated that a corresponding recessed surface 106 may be provided on the bottom of the opposite actuator 28 to provide for a complimentary fit. As best seen in FIG. 10C, one horizontal ramp 56 is positioned deeper than another horizontal ramp 56 to further facilitate this nesting configuration of the adjacent actuators 28. The horizontal ramps 90 of the actuators 28 slidably interface with the horizontal ramps 56 of the rear plate 22, thereby permitting lateral movement of the left and right side assemblies 12, 14. The actuators 28 may have features that engage with the mating rear plate 22 that limit the amount of translation while expanding in width. When expanded laterally in width, the actuators 28 slide outward and away from one another, thereby increasing the width of the implant 10. FIG. 10B shows the actuators 28 fully expanded in width.

Figure 11A:
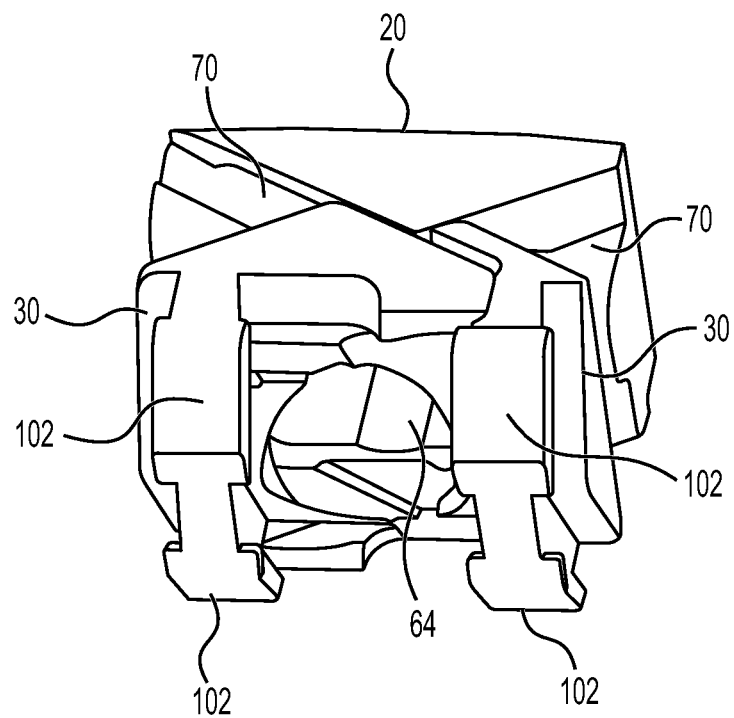
FIGS. 11A-11B illustrate the front ramps slidably engaged with the front plate in a collapsed position and expanded in width, respectively.
Figure 11B:
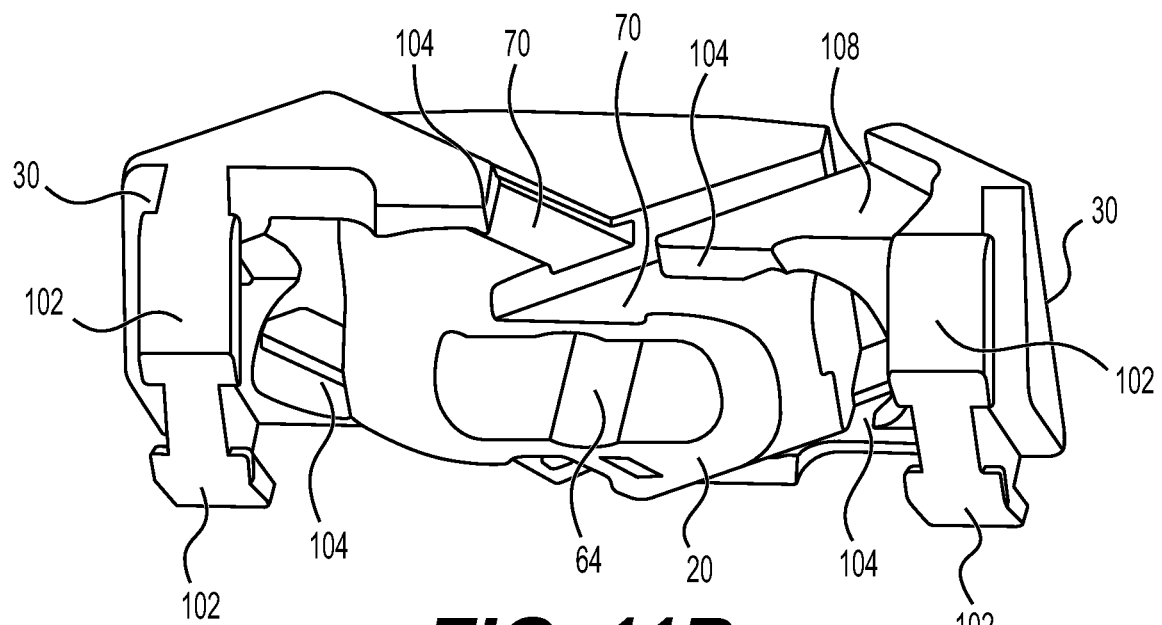

Front ramps 30 and front plate 20 utilize a similar sliding interface as actuators 28 and rear plate 22. FIGS. 11A-11B show the front ramps 30 slidably engaged with the front plate 20 in collapsed and expanded positions, respectively. Front ramps 30 slide onto the front plate 20 by aligning keying features that control expansion. In FIG. 11A, the front ramps 30 are engaged with the front plate 20 and collapsed onto one another. A recessed surface 108 on top of one front ramp 30 sized and dimensioned to receive the other front ramp 30 permits the front ramps 30 to nest together, thereby providing a small footprint for insertion. It will be appreciated that a corresponding recessed surface 108 may be provided on the bottom of the opposite front ramp 30 to provide for a complimentary fit. Similar to rear ramp 22, one horizontal ramp 70 may be positioned at a depth greater than the other horizontal ramp 70 to further facilitate this nesting configuration of the front ramps 30. The horizontal ramps 104 of the front ramps 20 slidably interface with the horizontal ramps 70 of the front plate 20. The front ramps 20 may have features that engage with the mating front plate 20 that limit the amount of translation while expanding in width. In FIG. 11B, the actuators 28 are fully expanded in width. When expanded in width, the front ramps 20 slide outward and away from one another, thereby increasing the overall width of the implant 10.

Turning now to FIGS. 12 and 13A-13D, the implant assembly 10 may include endplate clip 32 to keep the assembly from expanding in height until the full width expansion is achieved. When the assembly is fully contracted, the endplate clip 32 is engaged into all of the endplates 24, 26. Once the assembly fully expands in width, the endplate clip 32 is no longer engaged with endplates 24, 26 and allows the assembly 10 to also expand in height.

Figure 12:
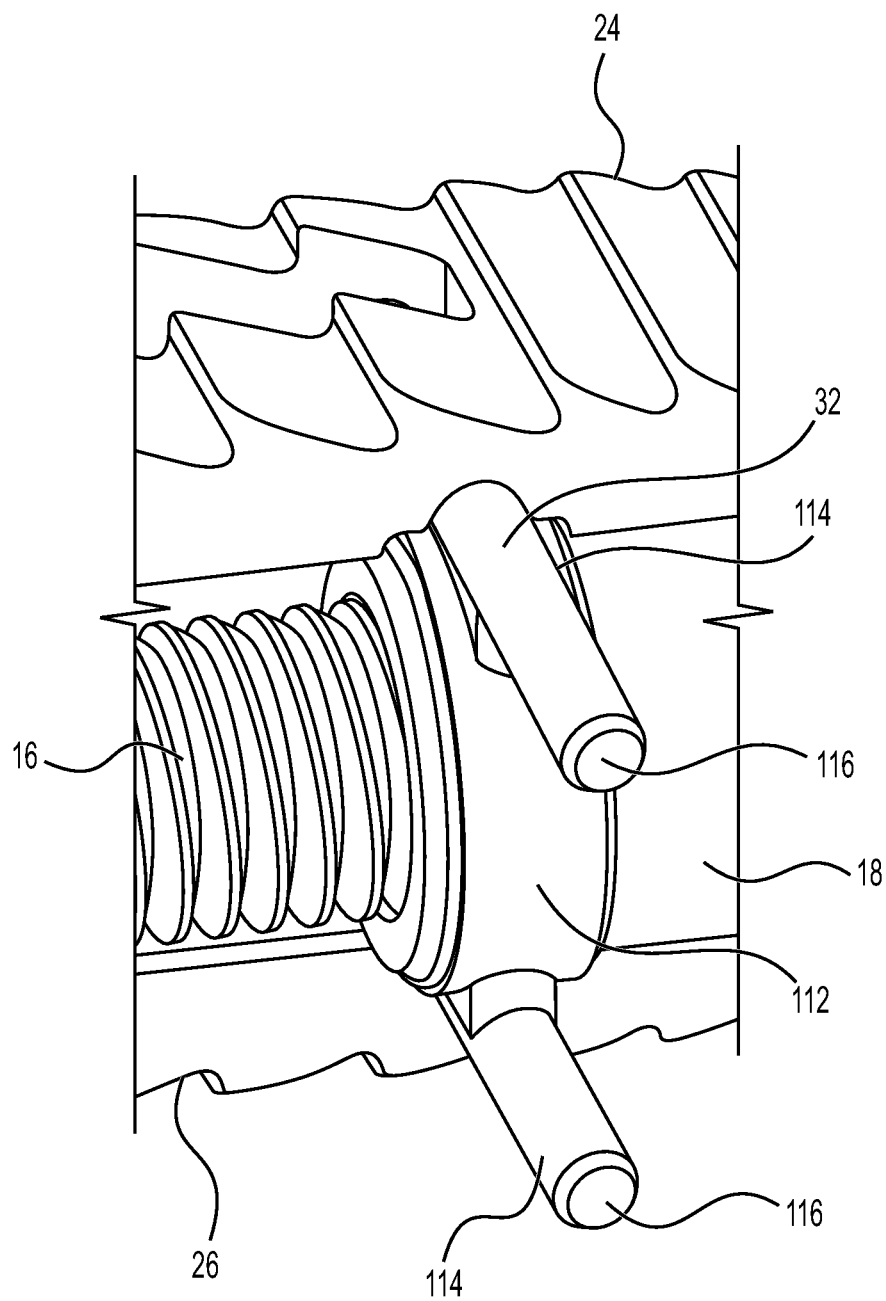
FIG. 12 shows an endplate clip positioned around the drive sleeve configured to prevent the side assemblies from expanding in height until fully expanded in width according to one embodiment (the second set of endplates are omitted for clarity)

As best seen in FIG. 12, the endplate clip 32 may include a ring 112 configured to fit over the drive sleeve 18 and a plurality of posts 114 configured to engage the upper and lower endplates 24, 26. The ring 112 may include a full ring defining a central bore sized and dimensioned to snuggly fit around the tubular body of the drive sleeve 18. The posts 114 extend from the ring 112 and terminate at one or more free ends 116. For example, a first post 114 may be positioned above the ring 112 with two opposed free ends 116 extending into the left and right upper endplates 24, respectively, and a second post 114 may be positioned below the ring 112 with two opposed free ends 116 extending into the left and right lower endplates 26, respectively. The two posts 114 may be aligned in parallel, for example, horizontally in line with the upper and lower endplates 24, 26. Alternatively, four separate posts 114 may extend from the ring 112 and terminate at free ends 116 each receivable in the respective endplates 24, 26. It will be appreciated that the ring 112 may be substituted with another suitable attachment mechanism to the drive sleeve 18 and any suitable number and configuration of posts 114 or other configurations for the endplate clip 32 may be used to secure the endplates 24, 26 until fully expanded in width.

Figure 13A:
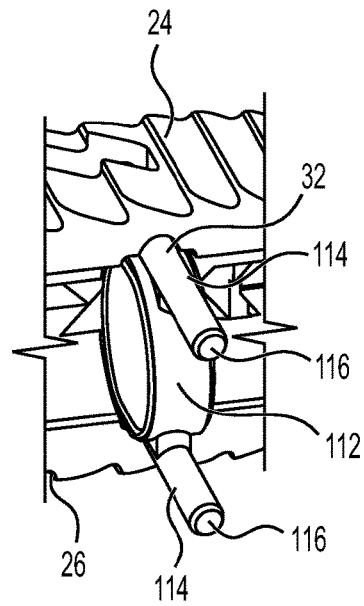
FIGS. 13A-13D shows the endplate clip engaged and disengaged from the endplates, respectively (the second set of endplates and the drive sleeve are omitted for clarity)
Figure 13B:
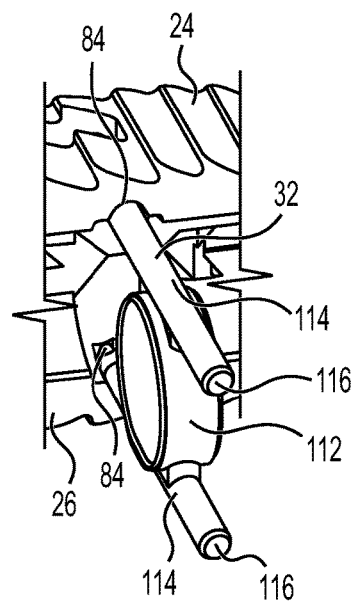
Figure 13C:
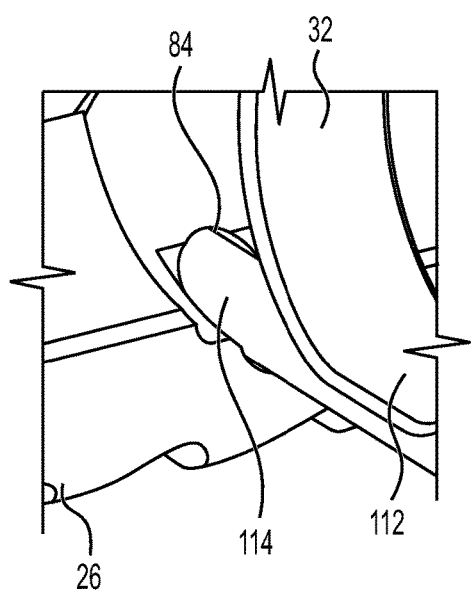
Figure 13D:
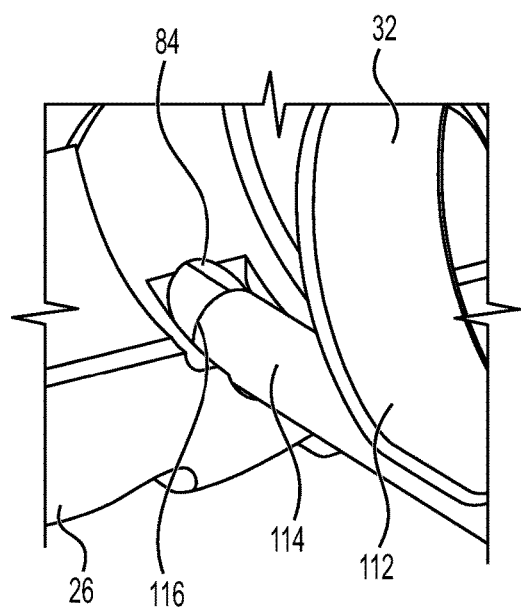
Figure 14:
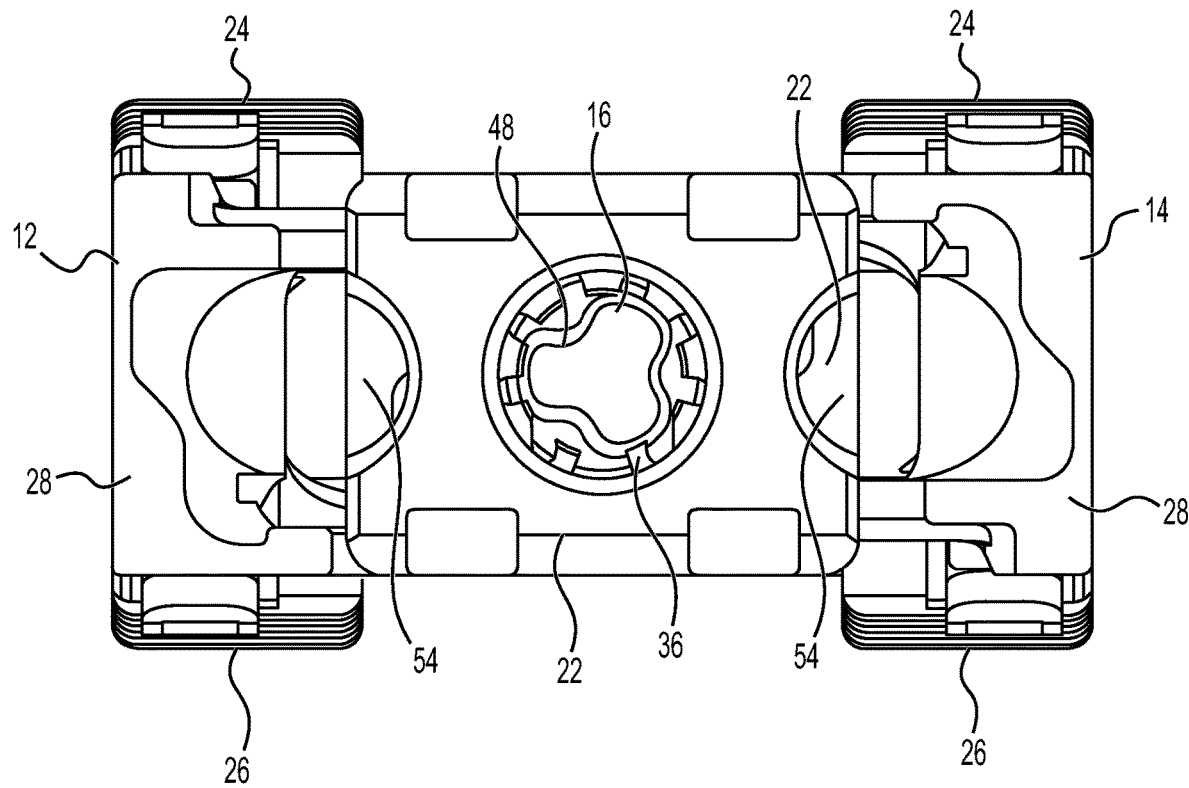
FIG. 14 is a rear view of the assembly expanded in width and height according to one embodiment.

FIGS. 13A and 13C show the endplate clip 32 and one set of endplates 24, 26 (the opposite set of endplates are omitted for clarity) before the left and right side assemblies 12, 14 are fully expanded in width. In the collapsed configuration or before fully expanded, the ends 116 of the posts 114 are received in the bores 84 through the side wall 78 of the endplates 24, 26. When the posts 114 are positioned in bores 84, the endplates 24, 26 are unable to expand in height. FIGS. 13B and 13D show the endplate clip 32 disengaged from the endplates 24, 26. Once fully expanded in width, the endplates 24, 26 move outward and away from one another and the ends 116 of the posts 114 are released from the bores 84. The endplates 24, 26 are then free to expand in height. FIG. 14 shows a rear view of the assembled implant 10 fully expanded in width and in height. The rear plate 22 defines recesses 54 and the actuators 28 allow entry to a central portion of the implant 10 to allow delivery of graft material into the implant 10 once fully expanded in width.

Figure 15A:
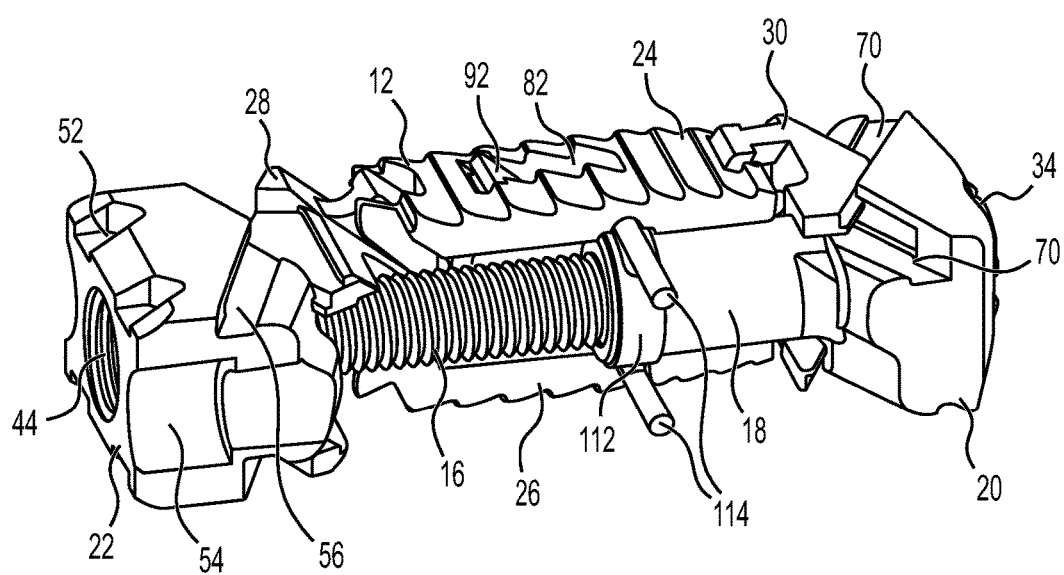
FIGS. 15A-15C shows the implant in a fully collapsed position, fully expanded in width, and fully expanded in width and height, respectively (one side assembly including one set of endplates, actuator, and front ramp are omitted for clarity)
Figure 15B:
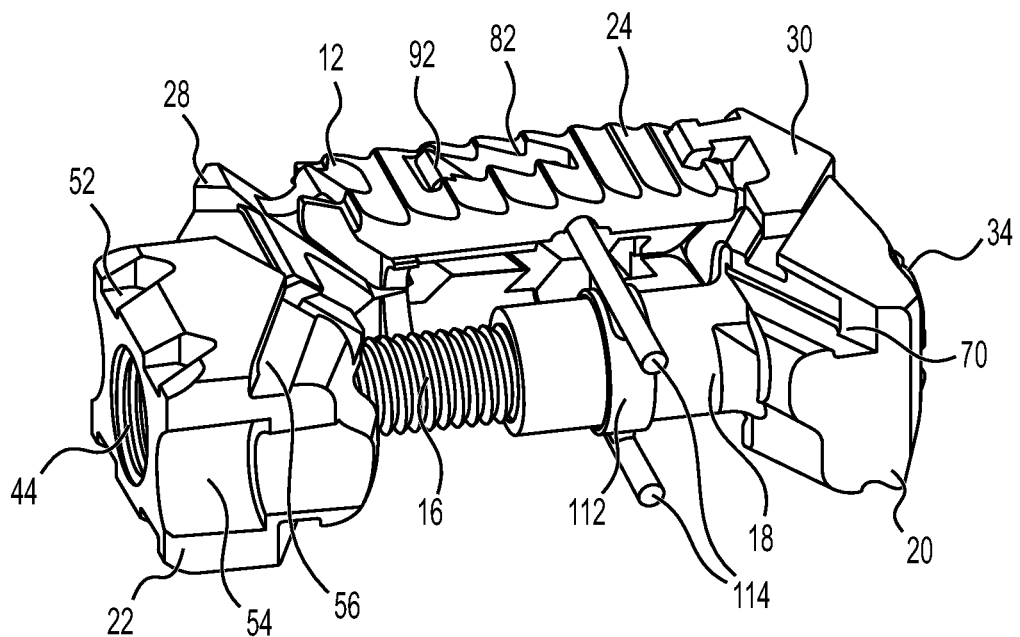
Figure 15C:
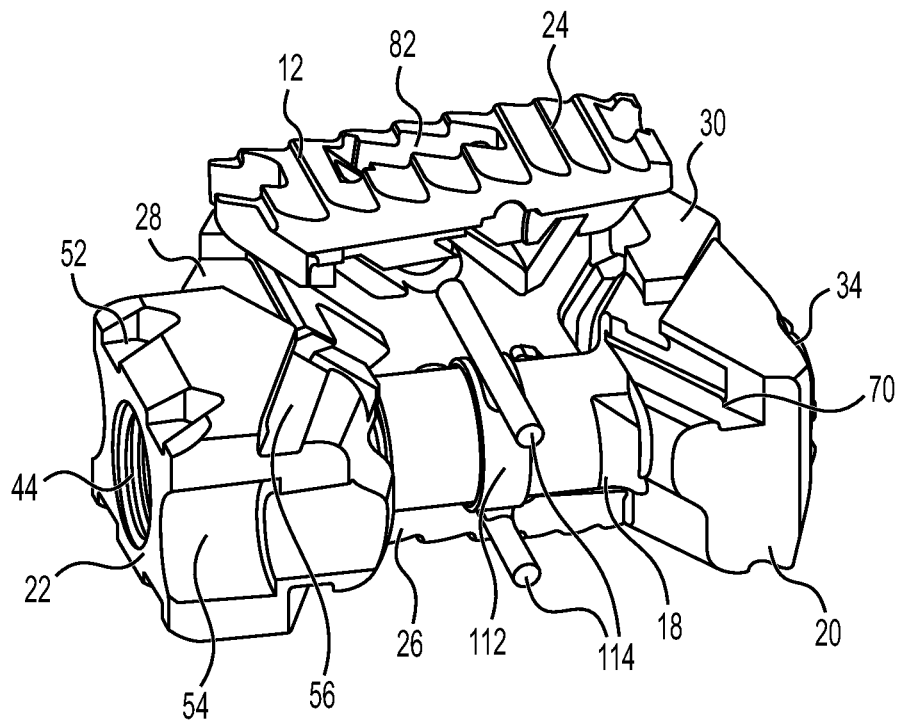

FIGS. 15A-15C show the implant 10 with the right side assembly 14 (one set of endplates 24, 26, actuator 28, and front ramp 30 and hidden for clarity). In FIG. 15A, the implant 10 is fully collapsed and may be inserted into a disc space, for example, through a posterior approach. The implant 10 may be attached to a multi-component instrument, for example, and a driving instrument may be used to engage the recess 48 in the drive screw 16 with a compatible drive feature. When the drive screw 16 is rotated, the screw 16 pulls and translates the screw sleeve 18, attached front plate 20, and attached front ramps 30 proximally. When doing so, it will force the front ramps 30 to translate outward and expand in width. Height expansion does not occur yet because the endplate clip 32 holds the endplates 24, 26 in place until full width expansion occurs. FIG. 15B shows the implant 10 fully expanded in width. Once the front ramps 30 are translated outward and full width expansion occurs, the front ramps 30 continue to translate with the screw sleeve 18 and attached front plate 20 proximally, thereby forcing the ramp features 80, 92, 102 of the actuators 28, front ramps 30, and endplates 24, 26 to translate the endplates 24, 26 upward and downward, respectively. FIG. 15C show the implant 10 fully expanded in width and in height. The amount of height of expansion on the left and right side assemblies 12, 14 may be the same or different. In this manner, the implant 10 is expanded in width for an increased footprint to aid in overall stability and the implant 20 is adjusted in lordosis and height for a precise patient fit.

In one embodiment, the implant 10 may be assembled as follows. The two front ramps 30 are placed onto front plate 20 by aligning the ramp/sliding features 70, 104. The two actuators 28 are placed onto rear plate 22 by aligning the ramp/sliding features 56, 90. The left and right sides 12, 14 are each assembled as follows. The lower endplate 26 is placed onto actuator 28. The upper endplate 24 is placed onto actuator 28. The front ramp 30 is placed into both the lower and upper endplates 24, 26. Alternatively, the upper endplate 24 is placed onto the actuator and the front ramp 20 is placed onto the upper endplate 24. Then the lower endplate 26 is placed onto both the actuator 28 and the front ramp 20 while ensuring all ramps 80, 92, 102 are engaged with each other. Next, the threaded sleeve 18 is inserted into the front plate 20 and secured with the lock nut 34. The endplate clip 32 is slid onto the threaded sleeve 18 to engage four posts 114 into the bores 84 of the endplates 24, 26. The PEEK ring 38 is assembled onto the drive screw 16 which are then inserted through the rear plate 22, threaded into drive sleeve 18, and retained by the lock ring 36.

Figure 16A:
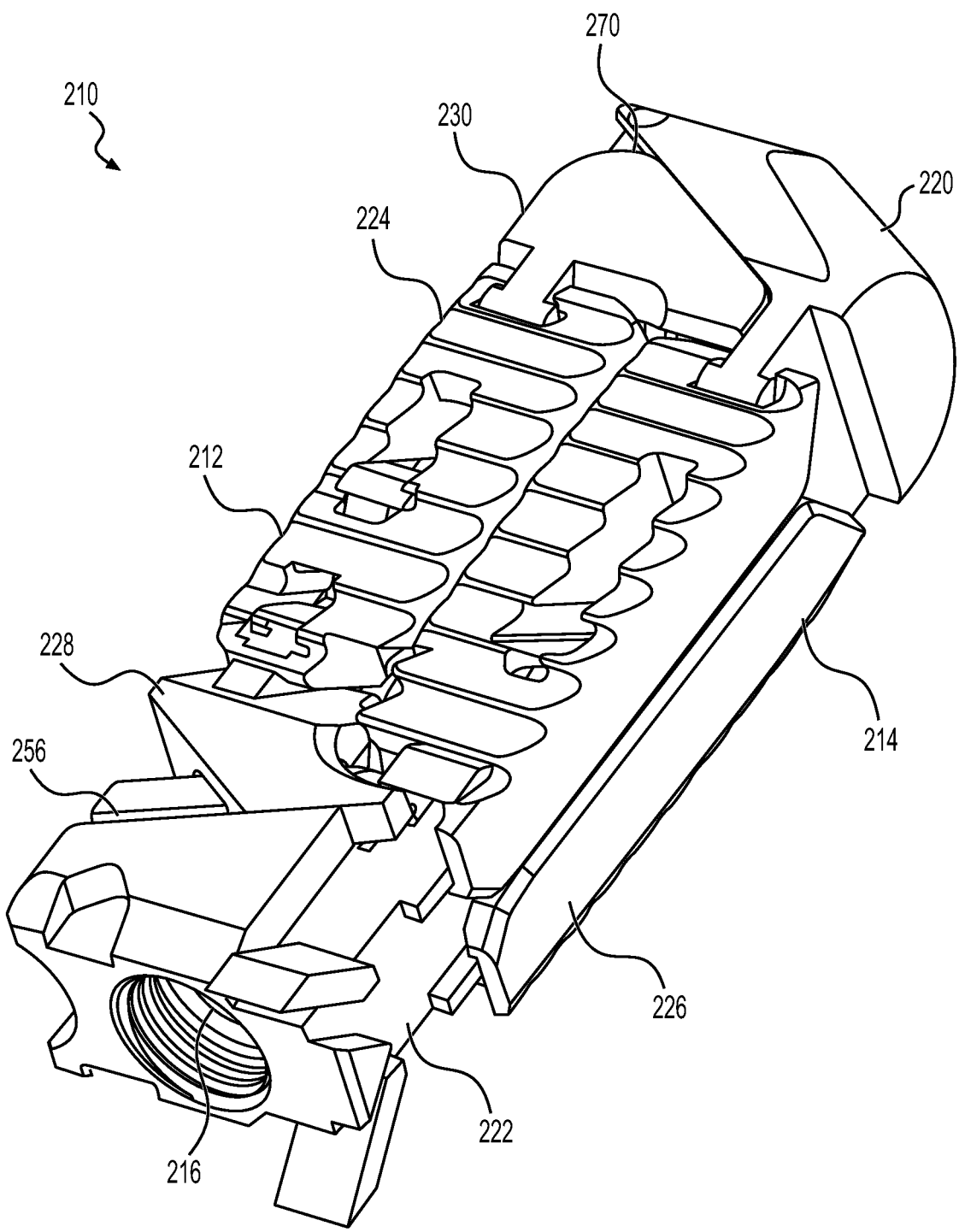
FIGS. 16A-16C illustrate an expandable implant in a collapsed position, one side expanded in width, and both sides expanded in height, respectively, according to one embodiment.
Figure 16B:
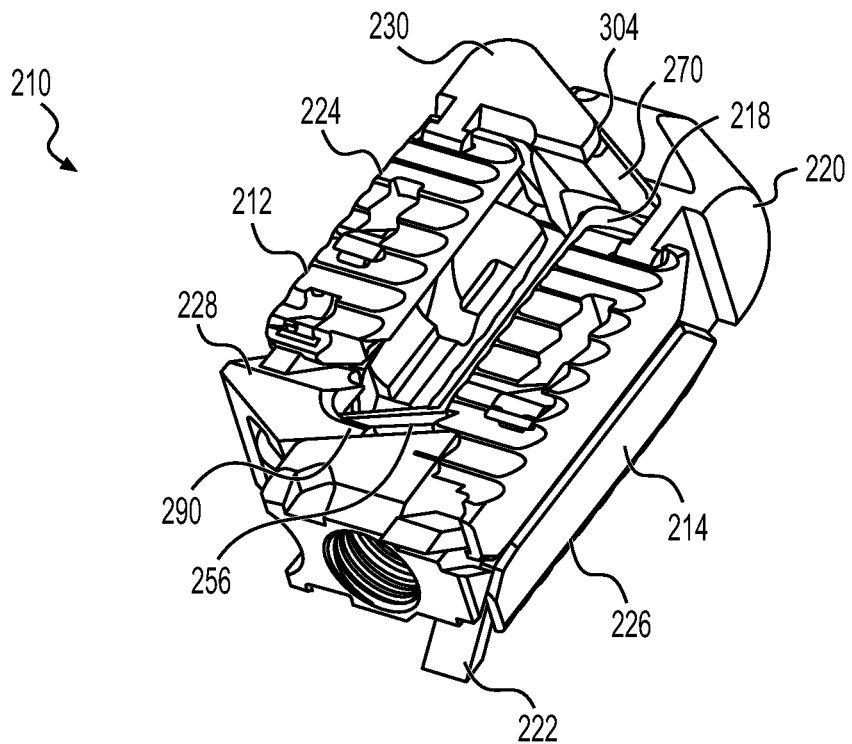
Figure 16C:
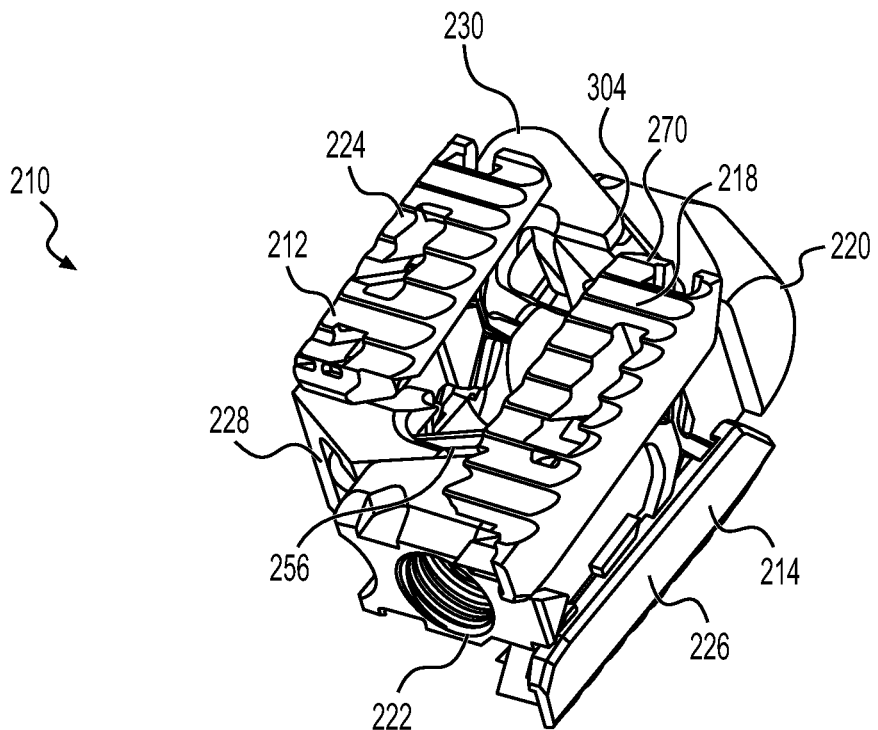

Turning now to FIGS. 16A-16C, expandable fusion device or implant 210 is similar to implant 10 except only one of the side portion assemblies 212 is configured to expand in width and the other 214 remains stationary. Implant 210 includes a first half or left side portion 212, which is moveable to expand in width and a second half or right side portion 214, which does not expand in width. Both of the left and right side portions 212, 214 expand in height. Although side portion 212 is shown as moveable and side portion 214 as stationary, it will be appreciated that the configuration may be reversed.

The left and right assemblies 212, 214 are controllable by a central drive screw 216 which is attached to a drive sleeve 218, a front distal plate 220 and a rear proximal plate 222. The drive screw 216 pulls the distal plate 220 towards the proximal plate 222 and pushes only one side portion 212 outwards with the use of ramps/slide mechanisms 256, 270, 290, 304. In the same manner as implant 10, the rear plate 222 includes a female horizontal ramp 256 slidably engaged with a male horizontal ramp 290 on the actuator 228 and the front plate 220 includes a female horizontal ramp 270 slidably engaged with a male horizontal ramp 304 on the front ramp 230. In this embodiment, the front and rear plates 220, 222 include only a single horizontal ramp 256, 270 on each of the top and bottom faces of the plates 220, 222 to engage with a single actuator 228 and front ramp 230, respectively.

Once the single side 212 is fully expanded in width, the front distal plate 220 continues to travel toward the proximal plate 222 as the drive screw 216 is rotated. The implant 210 may include an endplate clip, similar to endplate clip 32, with posts to engage only the moveable side 212. Similar to implant 10, the single side 212 that expands outwards includes upper and lower endplates 224, 224, actuator 228, and front ramp 230, which is configured to expand in height via internal vertical ramps. The front distal plate 220 along with the single front ramp 230 is actuated while the drive screw 216 is turned. This actuation pulls the front plate 220 and front ramp 230 toward the proximal plate 222 and the single actuator 228, which then expands the top and bottom endplates 224, 226 with mating ramp features on the front ramp 230 and actuator 228. The single side 214 that does not expand laterally outward has incorporated the front ramp features into the front distal plate 220 and the actuator features into the rear proximal plate 222. Thus, the non-expanding side 214 includes upper and lower endplates 224, 226 directly engaged with ramps on the front and rear plates 220, 222. In particular, the front distal plate 220 includes one or more vertical ramps, similar to ramps 102, configured to slidably interface with the vertical ramps of the endplates 224, 226. Similarly, the rear plate 222 has an enlarged body with one or more vertical ramps, similar to ramps 92, configured to slidably interface with the vertical ramps of the endplates 224, 266. This allows the endplates 224, 226 on the non-width expanding side 214 to also expand in height. The amount of height of expansion on the expanding side 212 and non-expanding side 214 may be the same or different.

Although the invention has been described in detail and with reference to specific embodiments, it will be apparent to one skilled in the art that various changes and modifications can be made without departing from the spirit and scope of the invention. Thus, it is intended that the invention covers the modifications and variations of this invention provided they come within the scope of the appended claims and their equivalents. It is expressly intended, for example, that all components of the various devices disclosed above may be combined or modified in any suitable configuration.

What is claimed is:

1. An expandable intervertebral implant comprising:
   front and rear plates each having horizontal ramps;
   a central drive screw threadedly engaged with a drive sleeve, for moving the front plate relative to the rear plate; and
   left and right side portion assemblies each including upper and lower endplates having vertical ramps, an actuator having horizontal ramps slidably engaged with the horizontal ramps of the rear plate and vertical ramps slidably engaged with the vertical ramps of the upper and lower endplates, and a front ramp having horizontal ramps slidably engaged with the horizontal ramps of the front plate and vertical ramps slidably engaged with the vertical ramps of the upper and lower endplates,
   wherein rotation of the drive screw expands the implant in width and then in height
   wherein a distal end of the drive sleeve includes an exterior threaded portion receivable through a bore defined through the front plate, wherein a lock nut is coupled to the threaded portion of the drive sleeve, thereby securing the drive sleeve to the front plate
   wherein the drive sleeve includes a pair of keys on an outer surface of the drive sleeve configured to mate with a pair of keyways in the bore of the front plate, thereby preventing the drive sleeve from rotating.

2. The expandable intervertebral implant of claim 1, wherein the rear plate includes a pair of female horizontal ramps defined into top and bottom surfaces of the rear plate, and the actuator includes a pair of horizontal male ramps configured to interface with the female horizontal ramps of the rear plate.

3. The expandable intervertebral implant of claim 2, wherein the horizontal ramps of the rear plate are slanted such that one end of each ramp starts at a side of the rear plate and extends toward a center of the rear plate with the horizontal ramps leading toward one another.

4. The expandable intervertebral implant of claim 2, wherein one of the female horizontal ramps has a depth greater than the other female horizontal ramp.

5. The expandable intervertebral implant of claim 1, wherein the front plate includes a pair of female horizontal ramps defined into top and bottom surfaces of the front plate, and the front ramp includes a pair of male horizontal ramps configured to interface with the female horizontal ramps of the front plate.

6. The expandable intervertebral implant of claim 5, wherein the horizontal ramps of the front plate are slanted such that one end of each ramp starts at a side of the front plate and extends toward a center of the front plate with the horizontal ramps leading toward one another.

7. The expandable intervertebral implant of claim 5, wherein one of the female horizontal ramps has a depth greater than the other female horizontal ramp.

8. An expandable intervertebral implant comprising:
   a front plate having at least one ramp and a rear plate having at least one ramp;
   a central drive screw threadedly engaged with a drive sleeve, the central drive screw retained in the rear plate and the drive sleeve retained in the front plate;
   a left side portion assembly and a right side portion assembly, wherein the left and right side portion assemblies each include an upper endplate, a lower endplate, an actuator, and a front ramp, wherein the actuator includes a ramp slidably engaged with the ramp of the rear plate, and the front ramp includes a ramp slidably engaged with the ramp of the front plate,
   wherein rotation of the drive screw moves the front plate toward the rear plate and the ramp of the actuator slides across the ramp of the rear plate, and the ramp of the front ramp slides across the ramp of the front plate, thereby expanding a width of the implant
   wherein a distal end of the drive sleeve includes an exterior threaded portion receivable through a bore defined through the front plate, wherein a lock nut is coupled to the threaded portion of the drive sleeve, thereby securing the drive sleeve to the front plate
   wherein the drive sleeve includes a pair of keys on an outer surface of the drive sleeve configured to mate with a pair of keyways in the bore of the front plate, thereby preventing the drive sleeve from rotating.

9. The expandable intervertebral implant of claim 8, wherein the ramps of the front plate and the rear plate include horizontal ramps aligned along one or more horizontal planes.

10. The expandable intervertebral implant of claim 8, wherein the rear plate includes a pair of female ramps defined into top and bottom surfaces of the rear plate, and the actuator includes a pair of male ramps configured to interface with the female ramps of the rear plate.

11. The expandable intervertebral implant of claim 8, wherein the front plate includes a pair of female ramps defined into top and bottom surfaces of the front plate, and the front ramp includes a pair of male ramps configured to interface with the female ramps of the front plate.

12. The expandable intervertebral implant of claim 8, wherein the left and right side portion assemblies have a laterally collapsed configuration having a first width and a laterally expanded configuration having a second width, and wherein the left and right side portion assemblies have a vertically collapsed configuration having a first height and a vertically expanded configuration having a second height.

13. The expandable intervertebral implant of claim 12, wherein rotation of the drive screw moves the front plate toward the rear plate, thereby first transitioning the left and right side portion assemblies to the laterally expanded configuration and then to the vertically expanded configuration.

14. The expandable intervertebral implant of claim 8, wherein the drive sleeve includes a tubular body with an internally threaded bore, and the central drive screw includes an externally threaded shaft allowing for threaded engagement with the internally threaded bore of the drive sleeve.

* * * * *